US009058737B2

(12) United States Patent
Nakai et al.

(10) Patent No.: US 9,058,737 B2
(45) Date of Patent: Jun. 16, 2015

(54) WAKEFULNESS-MAINTAINING DEVICE AND WAKEFULNESS-MAINTAINING METHOD

(75) Inventors: Wataru Nakai, Tokyo (JP); Hiroyuki Kubotani, Hyogo (JP); Takeshi Toi, Tokyo (JP); Masayuki Satomi, Tokyo (JP)

(73) Assignee: Chuo University, Tokyo (JP)

( * ) Notice: Subject to any disclaimer, the term of this patent is extended or adjusted under 35 U.S.C. 154(b) by 43 days.

(21) Appl. No.: 14/117,855

(22) PCT Filed: Mar. 1, 2012

(86) PCT No.: PCT/JP2012/001407
§ 371 (c)(1),
(2), (4) Date: Nov. 15, 2013

(87) PCT Pub. No.: WO2012/157156
PCT Pub. Date: Nov. 22, 2012

(65) Prior Publication Data
US 2014/0104064 A1      Apr. 17, 2014

(30) Foreign Application Priority Data
May 16, 2011   (JP) .................................. 2011-109201

(51) Int. Cl.
*G08B 23/00*        (2006.01)
*G08B 21/06*        (2006.01)
(Continued)

(52) U.S. Cl.
CPC ............... *G08B 21/06* (2013.01); *A61M 21/00* (2013.01); *A61M 2021/0027* (2013.01); *A61M 2205/3375* (2013.01); *H04R 3/00* (2013.01); *H04R 2499/13* (2013.01)

(58) Field of Classification Search
CPC ..................... A61M 21/00; A61M 2021/0027; A61M 2021/0083; A61M 2205/3375; G08B 21/06; B60K 28/06
USPC ................................... 340/575, 576; 180/272
See application file for complete search history.

(56) References Cited

U.S. PATENT DOCUMENTS 5,923,256 A *  7/1999  Satake et al. .................. 340/575
5,952,929 A *  9/1999  Yasushi et al. ................ 340/575
(Continued)

FOREIGN PATENT DOCUMENTS

JP        08-196637 A       8/1996
JP        2004-254750 A     9/2004
(Continued)

*Primary Examiner* — Eric M Blount
(74) *Attorney, Agent, or Firm* — Brundidge & Stanger, P.C.

(57) ABSTRACT

A wakefulness-maintaining device capable of maintaining a driver's wakefulness by making the driver aware of changes in sound characteristics. A wakefulness-maintaining device (100), which maintains a person's wakefulness, wherein: a switching time control part (102) analyzes the characteristics of perceived sounds acquired by a microphone provided inside the vehicle, the perceived sounds comprising control sounds played back by the wakefulness-maintaining device (100) and environmental sounds around the person when no control sounds are being played back; an in-car sound-accumulating part (103) accumulates the perceived sounds; an acoustic pressure change-setting part (105) sets the control method to be used on the environmental sounds on the basis of the characteristics of the perceived sounds accumulated by the in-car sound-accumulating part (103); and a control sound-generating part (106) applies the control method, set by the acoustic pressure change-setting part (105), on the environmental sounds and generates control sounds.

13 Claims, 15 Drawing Sheets

(51) Int. Cl.
*A61M 21/00* (2006.01)
*H04R 3/00* (2006.01)

(56) References Cited

U.S. PATENT DOCUMENTS

| | | | |
|---|---|---|---|
| 6,461,316 B1* | 10/2002 | Lee et al. | 601/46 |
| 2008/0204256 A1* | 8/2008 | Omi | 340/575 |
| 2012/0200414 A1* | 8/2012 | White et al. | 340/575 |
| 2012/0212353 A1* | 8/2012 | Fung et al. | 340/905 |
| 2013/0069788 A1* | 3/2013 | Chang | 340/575 |

FOREIGN PATENT DOCUMENTS

| | | |
|---|---|---|
| JP | 2007-260015 A | 10/2007 |
| WO | 2006-109390 A1 | 10/2006 |

* cited by examiner

| FREQUENCY DISTRIBUTION OF ACCUMULATED VEHICLE INTERIOR SOUND IN PERIOD ONE PERIOD BEFORE RELATIVE TO REFERENCE FREQUENCY DISTRIBUTION | | CANDIDATE SOUND PRESSURE CHANGE METHODS | |
|---|---|---|---|
| ROAD NOISE | WIND NOISE | ROAD NOISE | WIND NOISE |
| LARGE | LARGE | – | – |
| LARGE | SMALL | ATTENUATION | RAISE |
|  |  | – | RAISE |
| SMALL | LARGE | RAISE | ATTENUATION |
|  |  | RAISE | – |
| SMALL | SMALL | RAISE | RAISE |
|  |  | – | RAISE |

FIG. 5

| FREQUENCY DISTRIBUTION OF ACCUMULATED VEHICLE INTERIOR SOUND IN PERIOD ONE PERIOD BEFORE RELATIVE TO REFERENCE FREQUENCY DISTRIBUTION | | FREQUENCY DISTRIBUTION OF ACCUMULATED VEHICLE INTERIOR SOUND IN PERIOD TWO PERIODS BEFORE RELATIVE TO REFERENCE FREQUENCY DISTRIBUTION | | CANDIDATE SOUND PRESSURE CHANGE METHODS | |
|---|---|---|---|---|---|
| ROAD NOISE | WIND NOISE | ROAD NOISE | WIND NOISE | ROAD NOISE | WIND NOISE |
| LARGE | LARGE | LARGE | LARGE | | |
| | | LARGE | SMALL | ATTENUATION | ATTENUATION |
| | | SMALL | LARGE | ATTENUATION | ATTENUATION |
| | | SMALL | SMALL | ATTENUATION | — |
| | | NONE | NONE | — | ATTENUATION |
| LARGE | SMALL | LARGE | LARGE | ATTENUATION | ATTENUATION |
| | | LARGE | SMALL | ATTENUATION | RAISE |
| | | SMALL | LARGE | — | — |
| | | SMALL | SMALL | ATTENUATION | RAISE |
| | | NONE | NONE | ATTENUATION | RAISE |
| SMALL | LARGE | LARGE | LARGE | ATTENUATION | ATTENUATION |
| | | LARGE | SMALL | RAISE | — |
| | | SMALL | LARGE | RAISE | ATTENUATION |
| | | SMALL | SMALL | RAISE | ATTENUATION |
| | | NONE | NONE | — | RAISE |
| SMALL | SMALL | LARGE | LARGE | RAISE | — |
| | | LARGE | SMALL | RAISE | RAISE |
| | | SMALL | LARGE | RAISE | RAISE |
| | | NONE | NONE | RAISE | RAISE |

FIG. 9

WAKEFULNESS-MAINTAINING DEVICE AND WAKEFULNESS-MAINTAINING METHOD

TECHNICAL FIELD

The present invention relates to a wakefulness-maintaining apparatus and a wakefulness-maintaining method that suppress a decrease in wakefulness of a driver using ambient sound.

BACKGROUND ART

Driving on a monotonous road such as an expressway easily makes the driver drowsy. In other words, a decrease in wakefulness (arousal level) of the driver easily occurs.

As a technique of suppressing such decrease in wakefulness of a driver, a method including changing music characteristics at particular intervals has been proposed (see, for example, PTL 1). In PTL 1, one of sound characteristics that stimulate senses of a person is changed at regular or random intervals that are equal to or shorter than a half cycle of his/her sleep-wake rhythm to maintain wakefulness of a driver.

CITATION LIST

Patent Literature

PTL 1
Japanese Patent Application Laid-Open No. HEI 8-196637

SUMMARY OF INVENTION

Technical Problem

However, in PTL 1, assuming that one of sound characteristics to be changed is sound pressure, a preset sound pressure is changed by a fixed amount that is set in advance.

Therefore, if vehicle exterior sound is larger, the amount of change in sound pressure by the aforementioned method is relatively smaller and thus a driver less easily perceives the sound pressure change, which results in the problem of difficulty in obtaining a sufficient wakefulness maintenance effect.

An object of the present invention is to provide a wakefulness-maintaining apparatus and a wakefulness-maintaining method each of which makes a driver perceive a change in sound characteristics to maintain wakefulness of the driver.

Solution to Problem

A wakefulness-maintaining apparatus according to an aspect of the present invention is an apparatus for maintaining wakefulness of a person, the apparatus including: an analysis section that analyzes a characteristic of heard sound acquired via a microphone installed inside a vehicle, the heard sound containing control sound reproduced by the wakefulness-maintaining apparatus and ambient sound around the person in a state in which the control sound is not reproduced; an accumulation section that accumulates the heard sound analyzed by the analysis section; a setting section that sets a control method to be applied to the ambient sound, based on the characteristic of the heard sound accumulated by the accumulation section; and a generation section that generates the control sound by applying the control method set by the setting section to the ambient sound.

This configuration provides the ability of setting a control method to be applied to ambient sound next time, based on records of magnitude relationships in two or more particular frequency bands between sound pressures of heard sound and respective thresholds, which provides the advantage of being able to prevent a person from getting familiar with heard sound as a result of continuation of heard sound with a same frequency characteristic and a wakefulness decrease resulting from a person getting familiar with heard sound.

A wakefulness-maintaining apparatus according to an aspect of the present invention is an apparatus for maintaining wakefulness of a person, the apparatus including: an analysis section that analyzes a characteristic of heard sound around a person, the heard sound containing control sound reproduced by the wakefulness-maintaining apparatus and ambient sound around the person in a state in which the control sound is not reproduced; an accumulation section that accumulates the heard sound analyzed by the analysis section; a setting section that sets a control method to be applied to the ambient sound, based on the characteristic of the heard sound accumulated by the accumulation section; a generation section that generates the control sound by applying the control method set by the setting section to the ambient sound; a time setting section that sets sound familiarity obtainment time which is a period of time until the person becomes familiar with the heard sound, based on a result obtained by the analysis of the characteristic of the heard sound; and a time control section that controls a timing at which the control method is applied to the ambient sound.

This configuration provides the ability of setting a control method for ambient sound in consideration of a period of time until a person becomes familiar with heard sound before the person get familiar to the heard sound, which provides the advantage of provision of a wakefulness maintenance effect while suppressing annoyance due to frequent ambient sound switching.

Advantageous Effects of Invention

The present invention enables wakefulness of a driver to be maintained by making the driver perceive a change in sound characteristics.

BRIEF DESCRIPTION OF DRAWINGS

FIG. 5 is a diagram illustrating association relationships between accumulated vehicle interior sounds and candidate sound pressure change methods according to Embodiment 1 of the present invention;

FIG. 9 is a diagram illustrating association relationships between accumulated vehicle interior sounds and candidate sound pressure change methods according to Embodiment 2 of the present invention;

DESCRIPTION OF EMBODIMENTS

Figure 1:
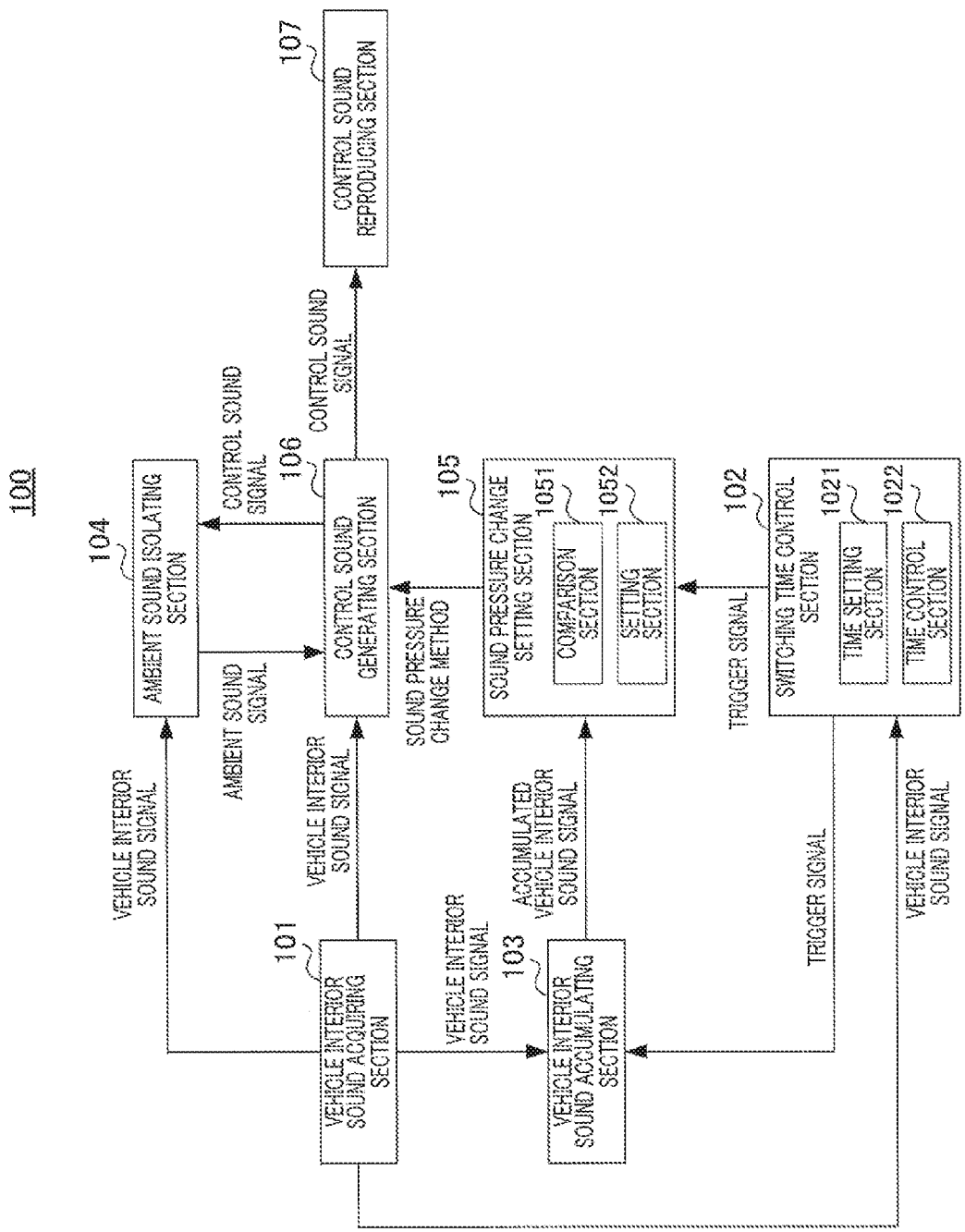
FIG. 1 is a block diagram illustrating a configuration of a wakefulness-maintaining apparatus according to Embodiment 1 of the present invention.

Embodiments of the present invention will be described in detail below with reference to the accompanying drawings. In the embodiments, same components are provided with same reference numerals and a description thereof will not be repeated to avoid overlap.

[Embodiment 1]
[Configuration of Wakefulness-Maintaining Apparatus 100]

FIG. 1 is a block diagram illustrating a configuration of wakefulness-maintaining apparatus 100 according to Embodiment 1 of the present invention. Embodiment 1 of the present invention indicates an example in which a wakefulness-maintaining apparatus and a wakefulness-maintaining method are applied to a vehicle. Wakefulness-maintaining apparatus 100 is installed in a vehicle to maintain wakefulness of a driver of the vehicle. In FIG. 1, wakefulness-maintaining apparatus 100 includes vehicle interior sound acquiring section 101, switching time control section 102, vehicle interior sound accumulating section 103, ambient sound isolating section 104, sound pressure change setting section 105, control sound generating section 106 and control sound reproducing section 107.

Vehicle interior sound acquiring section 101 acquires vehicle interior sound Sr using, for example, one or more microphones installed in the interior of the vehicle. Here, vehicle interior sound refers to sound to be heard by a driver inside the vehicle (heard sound), which is acquired by the microphone(s). Vehicle interior sound acquiring section 101 outputs acquired vehicle interior sound (vehicle interior sound signal) Sr to switching time control section 102, vehicle interior sound accumulating section 103, ambient sound isolating section 104 and control sound generating section 106.

The vehicle interior sound in Embodiment 1 is vehicle interior sound in normal running. Vehicle interior sound in normal running that a driver normally hears during driving on an expressway mainly contains road noise and wind noise. Road noise is sound generated by friction between tires of a vehicle and a road surface, which appears prominently in a frequency band of 100 to 500 Hz (hereinafter referred to as "road noise band"). Wind noise is sound generated as a result of the wind colliding with a running vehicle, which appears prominently in a frequency band of 1000 to 5000 Hz (hereinafter referred to as "wind noise band").

The road noise band and the wind noise band constantly and dominantly exist in a frequency distribution of sound existing under a monotonous driving environment that makes a driver drowsy. Thus, characteristics in the road noise band and the wind noise band can easily be changed at any timing. Furthermore, the road noise band and the wind noise band are less dependent on preference than vehicle interior sound that a driver actively hears such as music or the radio, and thus, individual differences in terms of the effect are less likely to appear. In addition, since road noise and wind noise are sounds naturally existing under a driving environment, a sense of discomfort is less likely to be given when changing characteristics of the sounds, and thus a sense of annoyance is less likely to occur. For the reasons described above, in sound pressure change setting section 105, sound pressures in the road noise band and the wind noise band are changed. A function of sound pressure change setting section 105 will be described later.

Switching time control section 102 sets switching time T, which is a period of time from a timing when one of characteristics (for example, a sound pressure) of vehicle interior sound was changed previously until the characteristic of vehicle interior sound is changed next time, based on vehicle interior sound Sr acquired by vehicle interior sound acquiring section 101. Switching time control section 102 controls set switching time T, and upon the elapse of switching time T, outputs a trigger signal to vehicle interior sound accumulating section 103 and sound pressure change setting section 105. After the output of the trigger signal to vehicle interior sound accumulating section 103 and sound pressure change setting section 105, switching time control section 102 sets switching time T again.

More specifically, switching time control section 102 includes time setting section 1021 and time control section 1022.

Time setting section 1021 acquires vehicle interior sound Sr from vehicle interior sound acquiring section 101. Time setting section 1021 analyzes a characteristic of acquired vehicle interior sound Sr, and calculates switching time T based on the analyzed characteristic of vehicle interior sound Sr. Tune setting section 1021 adjusts calculated switching time T. Time setting section 1021 sets adjusted switching time T as start time for a timer. When the timer in time control section 1022 reaches zero, time setting section 1021 acquires vehicle interior sound Sr again from vehicle interior sound acquiring section 101 and calculates switching time T.

The calculation of switching time T is performed based on at least one of frequency band, sound pressure variation, and pure tone component from among characteristics of vehicle interior sound Sr. In calculation of switching time T according to a frequency band, a period of time until a person becomes familiar with vehicle interior sound Sr (hereinafter referred to as "sound familiarity obtainment time") becomes longer as a sound pressure in a high-frequency band in vehicle interior sound Sr is higher, so that time setting section 1021 sets longer switching time T. In calculation of switching time T according to a sound pressure characteristic, since the sound familiarity obtainment time becomes longer as sound pressure variation of vehicle interior sound Sr is larger, time setting section 1021 sets longer switching time T. In calculation of switching time T according to pure tone components, since the sound familiarity obtainment time becomes longer as a ratio of pure tone components contained in vehicle interior sound Sr, which is obtained using, e.g., a tone to noise ratio, is larger, time setting section 1021 sets longer switching time T.

Here, evaluation values for relationships between four sound patterns with at least one of a sound pressure in a frequency band (40 to 500 Hz) of road noise components and a sound pressure in a frequency band (1 k to 5 kHz) of wind noise components increased/decreased relative to vehicle interior sound where a vehicle normally runs at 100 km/h and sound familiarity obtainment will be described.

The four sound patterns are vehicle interior sound 1, which is vehicle interior sound where a vehicle normally runs at 100 km/h, vehicle interior sound 2, which is sound resulting from attenuating a sound pressure in the road noise band of vehicle interior sound 1 by 6 dB, vehicle interior sound 3, which is sound resulting from raising a sound pressure in the wind noise band of vehicle interior sound 1 by 6 dB, vehicle interior sound 4, which is sound resulting from attenuating the sound pressure in the road noise band of vehicle interior sound 1 by 6 dB and raising the sound pressure in the wind noise band of vehicle interior sound 1 by 6 dB.

In a test, in a controlled state in which test subjects are not familiar with vehicle interior sounds 1 to 4, a minimum sound pressure width that the test subjects can sufficiently tell was set, the sound pressure of each of vehicle interior sounds 1 to 4 is varied to increase/decrease by the set sound pressure width for six seconds, and the test subjects perform the task of judging whether sound pressure variation occurs and whether the variation is an increase or a decrease by pressing buttons.

Figure 2:
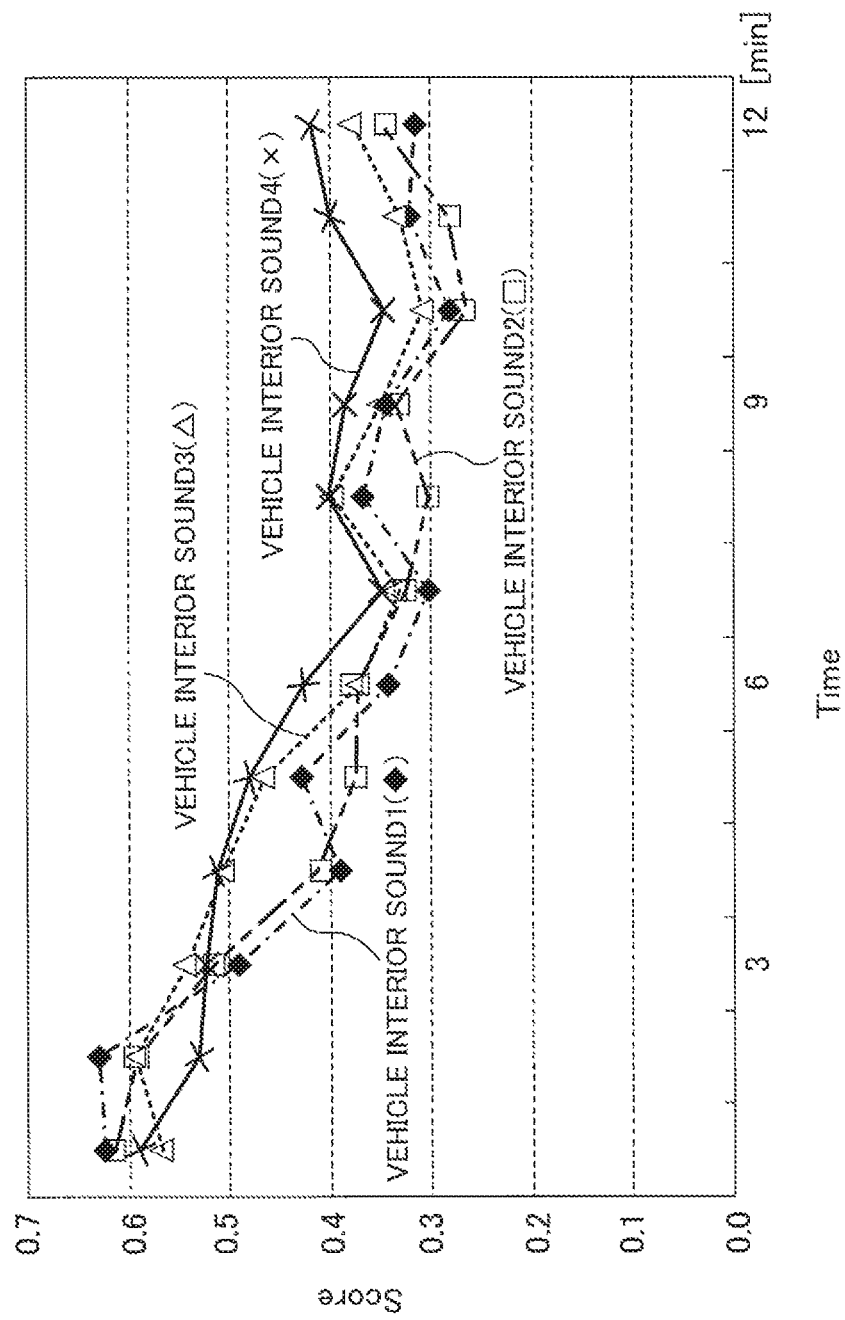
FIG. 2 is a diagram illustrating evaluation values relating to relationships between four sound patterns and obtainment of familiarity with the sounds according to Embodiment 1 of the present invention.

FIG. 2 illustrates results of analysis based on an average of all the test subjects for each vehicle interior sound. The ordinate axis (Score) indicates evaluation values expressed by Equation 1 and the abscissa axis (Time) indicates time.

[1]

$$E_n = C_n \times \left(\frac{I - R_n}{I}\right) \quad \text{(Equation 1)}$$

Here, Score En represents an evaluation value at evaluation timing (Time) n, Cn represents the percentage of correct answers in a task at evaluation timing n, I represents input wait time in the task, and Rn represents response time at evaluation timing n. From FIG. 2, while in the case of vehicle interior sounds 1 and 2, evaluation values below 0.4 were obtained approximately four minutes later from the start of the evaluation, in the case of vehicle interior sounds 3 and 4, evaluation values below 0.4 were obtained six to seven minutes later from the start of the evaluation. This indicates that as a sound pressure of a high frequency component of vehicle interior sound is higher, time consumed until obtainment of familiarity with the sound (sound familiarity obtainment time) is longer.

The adjustment of switching time T is performed based on either sensitivity to vehicle interior sound Sr or experience of hearing of ambient sound Se and vehicle interior sound Sr. Here, ambient sound Se is running sound generated while a vehicle is running. In adjustment of switching time T according to sensitivity to vehicle interior sound Sr, sensitivity to vehicle interior sound Sr is estimated from, e.g., age, mother tongue and/or living space, and the adjustment is performed based on the estimated sensitivity. In other words, in the case of an elderly person, the sensitivity to high frequency components (in particular, 1 kHz or higher) is low and sensitivity to wind noise components included in the relevant band is also low, and therefore, the sound familiarity obtainment time is adjusted to be short.

Also, while in the case of a person whose mother tongue frequently uses consonants (for example, English) is familiar with sounds of high frequency components (1.5 to 5 kHz in English) and the sensitivity to wind noise components is high, in the case of a person whose mother tongue frequently uses vowels (for example, Japanese) is familiar with sounds of relatively-low frequency components (500 Hz to 1.5 kHz) and the sensitivity to wind noise components is low. Accordingly, time setting section 1021 sets long sound familiarity obtainment time for the former person and sets short sound familiarity obtainment time for the latter person.

Also, in the case of a person that is familiar with an environment whose sound reflection coefficient is high, such as a person who lives in a dwelling having concrete or stone walls, such person is familiar with sounds of high frequency components and has high sensitivity to wind noise components, and thus, time setting section 1021 adjusts long sound familiarity obtainment time. Meanwhile, in the case of a person that is familiar with an environment whose sound absorption coefficient is high such as a person who lives in a Japanese traditional room, such person has relatively-low sensitivity to wind noise components, and thus, time setting section 1021 adjusts sound familiarity obtainment time to be short.

In other words, switching time control section 102 functions as a sensitivity estimating section that estimates sensitivity of a person that hears vehicle interior sound Sr (heard sound) to vehicle interior sound Sr. Time setting section 1021 adjusts the sound familiarity obtainment time according to the sensitivity of the person to vehicle interior sound Sr, which has been estimated by switching time control section 102.

In adjustment of switching time T according to experience of hearing of ambient sound Se, time setting section 1021 determines past experience of hearing of ambient sound Se, and adjusts the sound familiarity obtainment time to be longer as the experience of hearing of ambient sound Se is longer. In other words, since a person familiar with ambient sound Se that can be heard in an environment in which no wakefulness-maintaining apparatus operates such as a person who drives a same car for a long time or a person who often drives in a same area easily notices vehicle interior sound Sr created by a wakefulness-maintaining apparatus, and thus, time setting section 1021 adjust the sound familiarity obtainment time to be long.

In the case of adjustment of switching time T according to experience of hearing of vehicle interior sound Sr, time setting section 1021 determines past experience of hearing of vehicle interior sound Sr, and adjusts the sound familiarity obtainment time to be shorter as the experience of hearing of vehicle interior sound Sr is longer. In other words, a person who drives a vehicle with a wakefulness-maintaining apparatus installed therein for a long time is familiar with vehicle interior sound Sr and has low sensitivity to vehicle interior sound Sr, and thus, time setting section 1021 adjusts the sound familiarity obtainment time to be short.

In other words, switching time control section 102 functions as an experience determining section that determines experience of hearing of ambient sound and vehicle interior sound Sr (heard sound) for a person who hears the ambient sound and vehicle interior sound Sr (heard sound). Time setting section 1021 adjusts the sound familiarity obtainment time according to the person's experience of hearing at least the ambient sound or vehicle interior sound Sr, which is determined by switching time control section 102.

Here, switching time T may be a fixed value set in advance or a random value. Also, switching time T may be a value determined from biological information of a person. Examples of the value determined from biological information of a person include, e.g., a value inversely proportional to the content of alpha waves in brain waves. As a result of making switching time T be inversely proportional to the content of alpha waves in brain waves, where the wakefulness is low (the content of alpha waves is high), switching time T is short, enabling sound characteristics to be varied at a high frequency. Also, where the wakefulness is high (the content of alpha waves is low), switching time T is long, enabling sound characteristics to be varied at a low frequency.

Time control section 1022 starts the timer at the same time as time setting section 1021 sets switching time T as start time for the timer, and when the timer reaches zero (upon the elapse of switching time T), outputs a trigger signal for notification of the elapse of switching time T to vehicle interior sound accumulating section 103 and sound pressure change setting section 105. In other words, time control section 1022 controls a timing for sound pressure change setting section 105 to set a sound pressure change, the timing being provided each predetermined period of time.

Figure 3:
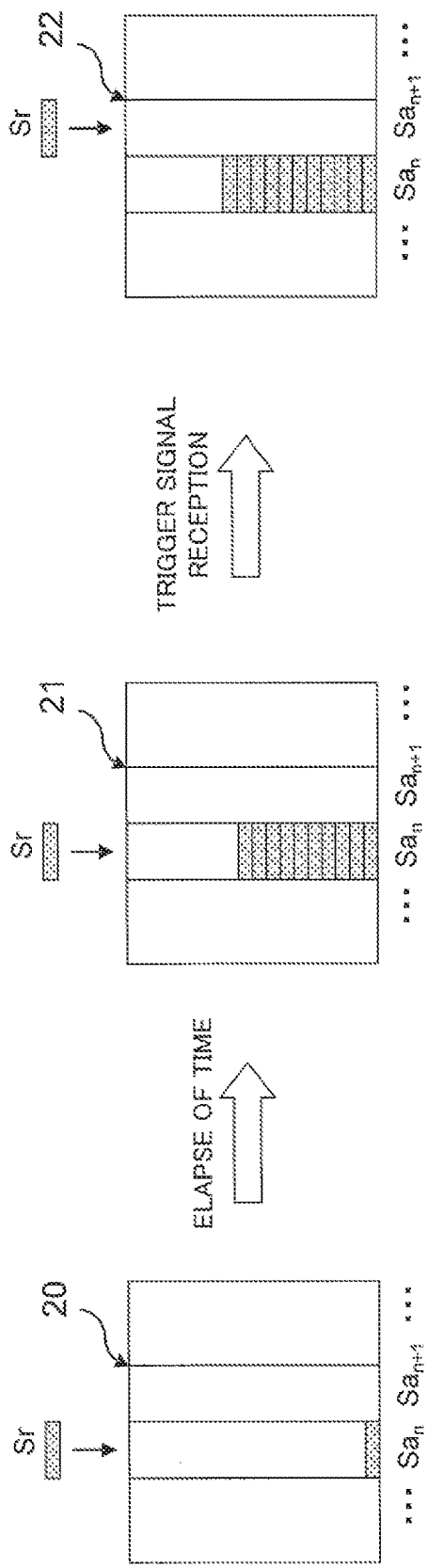
FIG. 3 is a diagram provided for description of processing in a vehicle interior sound accumulating section according to Embodiment 1 of the present invention.

Vehicle interior sound accumulating section 103 accumulates records of vehicle interior sound Sr acquired by vehicle interior sound acquiring section 101, according to the trigger signal input from switching time control section 102. FIG. 3 illustrates a manner in which vehicle interior sound accumulating section 103 accumulates vehicle interior sound Sr. As illustrated in FIG. 3, vehicle interior sound accumulating section 103 accumulates vehicle interior sound Sr acquired by vehicle interior sound acquiring section 101 as accumulated vehicle interior sound $Sa_n$ during a period from reception of a last trigger signal until reception of a next trigger signal (period from reception of a last trigger until the elapse of switching time T) (see reference numerals 20 and 21 in FIG. 3).

Upon reception of the trigger signal from switching time control section 102, vehicle interior sound accumulating section 103 terminates the accumulation of vehicle interior sound Sr as accumulated vehicle interior sound $Sa_n$, and starts new accumulation of vehicle interior sound Sr as accumulated vehicle interior sound $Sa_{n+1}$ (that is, accumulated vehicle interior sound in the next period) (see reference numeral 22 in FIG. 3). As described above, vehicle interior sound accumulating section 103 accumulates vehicle interior sound for each switching time T (predetermined period of time) as accumulated vehicle interior sound according to a trigger signal. Here, vehicle interior sound to be accumulated may be the sound itself or characteristics of the sound.

Ambient sound isolating section 104 generates ambient sound (ambient sound signal) Se based on the vehicle interior sound Sr acquired by vehicle interior sound acquiring section 101 and control sound (control sound signal) Sc generated by control sound generating section 106. Ambient sound isolating section 104 outputs generated ambient sound Se to control sound generating section 106. Here, control sound refers to sound generated by wakefulness-maintaining apparatus 100 (control sound generating section 106) in order to maintain wakefulness of a driver. Also, ambient sound refers to vehicle interior sound in a state in which no control sound is reproduced. In other words, a driver of a vehicle with wakefulness-maintaining apparatus 100 installed therein hears sound resulting from combination of control sound and ambient sound as vehicle interior sound.

More specifically, ambient sound isolating section 104 acquires vehicle interior sound Sr from vehicle interior sound acquiring section 101, and acquires control sound Sc generated immediately before from control sound generating section 106. Ambient sound isolating section 104 calculates control sound Sc' at a position of the microphone(s), using acquired control sound Sc and a transfer function for transfer between speakers and the microphone(s), which has been calculated in advance. The transfer function of transfer between the speakers and the microphone(s) is one indicating a manner of changing in sound characteristics output from the speakers at the position of the microphone(s), which is determined according to the shape of the vehicle. Ambient sound isolating section 104 extracts (isolates) sound resulting from removal of components of control sound Sc' at the microphone position from vehicle interior sound Sr, as ambient sound Se.

Upon input of the trigger signal from switching time control section 102, sound pressure change setting section 105 sets a sound pressure change method to be applied when generating next control sound Sc, based on accumulated vehicle interior sound $Sa_n$ accumulated in vehicle interior sound accumulating section 103. Sound pressure change setting section 105 outputs the set sound pressure change method to control sound generating section 106.

Specifically, sound pressure change setting section 105 includes comparison section 1051 and setting section 1052.

Comparison section 1051 compares sound pressures in two or more particular frequency bands of the vehicle interior sound (accumulated vehicle interior sound $Sa_n$) accumulated in vehicle interior sound accumulating section 103 with respective thresholds set in advance to determine magnitude relationships between the sound pressures in the respective particular frequency bands and the respective thresholds. In such case, comparison section 1051 determines the magnitude relationships between the sound pressures in the aforementioned particular frequency bands and the thresholds for each predetermined period of time, based on the trigger signal input from switching time control section 102. Then, comparison section 1051 holds the magnitude relationships (that is, records of the magnitude relationships) between the sound pressures in the respective particular frequency bands and the thresholds for each period of time.

Setting section 1052 sets a sound pressure change for each particular frequency band according to the record of the magnitude relationship for each particular frequency band, which has been determined in comparison section 1051. For example, setting section 1052 sets a sound pressure change method to raise (increase) a sound pressure in a frequency band (first frequency band) that is smaller than the threshold in a period one period before a current time (last period) from among the particular frequency bands. More specifically, where there is at least one particular frequency band whose sound pressure is smaller than the threshold in a period one period before a current time (last period) as a result of the comparison, setting section 1052 sets a sound pressure change method to raise the sound pressure in the at least one frequency band from among the particular frequency bands.

Control sound generating section 106 generates control sound Sc to be output from the speakers, based on ambient sound Se isolated by ambient sound isolating section 104 and the sound pressure change method determined by sound pressure change setting section 105. Then, control sound generating section 106 outputs generated control signal Sc to ambient sound isolating section 104 and control sound reproducing section 107. Specifically, control sound generating section 106 acquires ambient sound Se isolated by ambient sound isolating section 104 and also acquires the sound pressure change method set by sound pressure change setting section 105 to generate control sound Sc in order to reproduce sound obtained by applying the sound pressure change method to ambient sound Se (that is, sound whose sound pressure(s) in the aforementioned particular frequency band(s) has been changed) at the positions of the ears of a driver.

Control sound reproducing section 107 reproduces control sound Sc generated by control sound generating section 106, via speakers. As described above, control sound whose sound pressure has been changed according to a record of accumulated vehicle interior sound is output from the speakers of control sound reproducing section 107.

[Operation of Wakefulness-Maintaining Apparatus 100]

The operation of wakefulness-maintaining apparatus 100 having the above-described configuration will be described.

First, processing for setting a sound pressure change method in sound pressure change setting section 105 will be described.

Here, candidate sound pressure change methods where particular frequency bands in a frequency distribution (accumulated vehicle interior sound frequency distribution) $Fs_n$ of accumulated vehicle interior sound $Sa_n$ are two bands that are a road noise band and a wind noise band and sound pressures in these bands are changed relative to ambient sound to generate control sound are indicated.

Here, a frequency distribution of sound to be compared with accumulated vehicle interior sound (that is, threshold) in comparison section 1051 of sound pressure change setting section 105 is referred to as frequency distribution (reference frequency distribution) Fb of reference sound.

Accordingly, for each of the particular frequency bands (the road noise band and the wind noise band), "large" is indicated where a sound pressure in an accumulated vehicle interior sound frequency distribution is larger than a sound pressure in the reference frequency distribution, and "small" is indicated where a sound pressure in an accumulated vehicle interior sound frequency distribution is smaller than a sound pressure in the reference frequency distribution. Also, when generating next control sound Sc, "raising" is indicated where the sound pressure is increased, "attenuation" is indicated where the sound pressure is decreased, and "-" is indicated where no change is made to the sound pressure.

Figure 4:
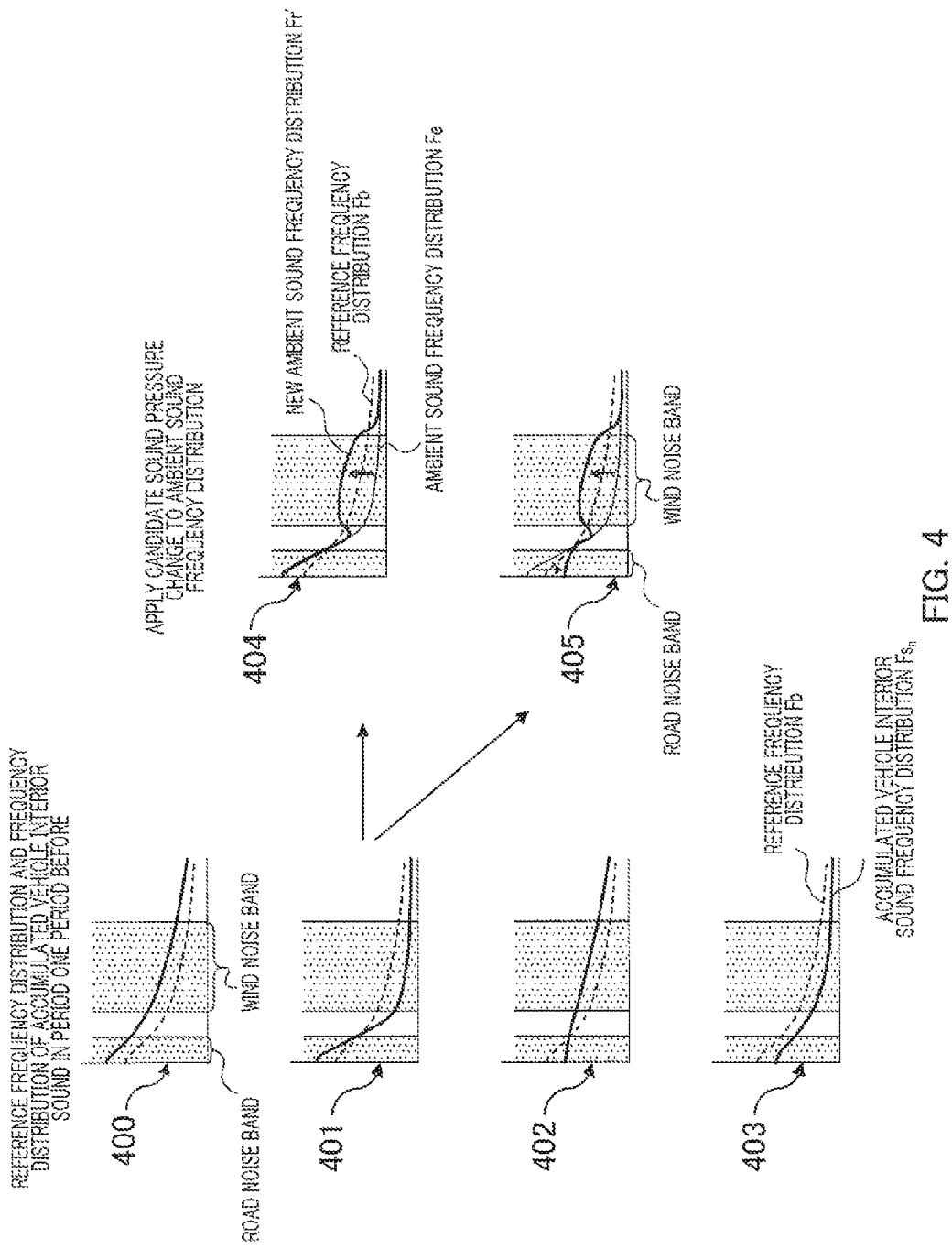
FIG. 4 is a diagram provided for description of processing in a sound pressure change setting section according to Embodiment 1 of the present invention.

FIG. 4 illustrates examples of processing for setting a sound pressure change method in sound pressure change setting section 105. In FIG. 4, the abscissa axis represents frequency and the ordinate axis represents sound pressure level.

Comparison section 1051 in sound pressure change setting section 105 compares sound pressures in a road noise band and a wind noise band in accumulated vehicle interior sound frequency distribution $Fs_n$ with sound pressures in the road noise band and the wind noise band in reference frequency distribution Fb, respectively. For example, in graph 401 illustrated in FIG. 4, the road noise band is "large" and the wind noise band is "small" in accumulated vehicle interior sound frequency distribution $Fs_n$ in the last period (which is a period one period before a current time).

Therefore, setting section 1052 in sound pressure change setting section 105 sets a sound pressure change method to raise the sound pressure in the wind noise band in accumulated vehicle interior sound frequency distribution $Fs_n$ that is smaller than the sound pressure in reference frequency distribution Fb. In other words, setting section 1052 selects either sound pressure change method (404) to "raise" the sound pressure in the wind noise band without changing the sound pressure in the road noise band, or sound pressure change method (405) to "attenuate" the sound pressure in the road noise band and "raise" the sound pressure in the wind noise band.

Although setting section 1052 in sound pressure change setting section 105 sets a sound pressure change method to "raise" or "attenuate" the sound pressure in the road noise band and the sound pressure in the wind noise band, setting section 1052 may set a sound pressure change method to "attenuate" or "raise" a sound pressure in a band other than the road noise band and the wind noise band.

Then, control sound generating section 106 applies to the sound pressure change method set by sound pressure change setting section 105 to frequency distribution (ambient sound frequency distribution) Fe of ambient sound Se, whereby frequency distribution (new vehicle interior sound frequency distribution) Fr' of new vehicle interior sound Sr' is provided at the position of the ears of the driver as indicated in graph 404 or 405 in FIG. 4. Control sound generating section 106 acquires vehicle interior sound Sr from the vehicle interior sound acquiring section, and calculates control sound Sc for making frequency distribution (vehicle interior sound frequency distribution) Fr of acquired vehicle interior sound Sr be the new vehicle interior sound frequency distribution. In new vehicle interior sound frequency distributions Fr' indicated in graphs 404 and 405 illustrated in FIG. 4, the respective sound pressures in the wind noise band, which are smaller than the sound pressure in reference frequency distribution Fb in the last period (one period before), are both raised to be equal or larger than the sound pressure in reference frequency distribution Fb.

Sound pressure change setting section 105 sets a sound pressure change method for each of accumulated vehicle interior sound frequency distributions $Fs_n$ (in graphs 400, 402 and 403) other than that indicated in graph 401, which are illustrated in FIG. 4, in a manner similar to that described above.

FIG. 5 is a table indicating a summary of association relationships between magnitude relationships ("large" or "small") between accumulated vehicle interior sound frequency distributions $Fs_n$ and reference frequency distribution Fb (threshold) in each of the road noise band and the wind noise band in the last period (one period before), and sound pressure change methods.

For example, as illustrated in FIG. 5, a case where the road noise band is "large" and the wind noise band is "small" in accumulated vehicle interior sound frequency distribution $Fs_n$ in the last period (one period before) (graph 401 illustrated in FIG. 4) is associated with a candidate sound pressure change method to "attenuate" the sound pressure in the road noise band and "raise" the sound pressure in the wind noise band (graph 405 illustrated in FIG. 4) or a candidate sound pressure change method that does not change the sound pressure in the road noise band and "raise" the sound pressure in the wind noise band (graph 404 illustrated in FIG. 4).

Likewise, as illustrated in FIG. 5, a case where the road noise band is "small" and the wind noise band is "large" in accumulated vehicle interior sound frequency distribution $Fs_n$ in the last period (one period before) (graph 402 illustrated in FIG. 4) is associated with a candidate sound pressure change method to "raise" the sound pressure in the road noise band and "attenuate" the sound pressure in the wind noise band or a candidate sound pressure change method to "raise" the sound pressure in the road noise band and not change the sound pressure in the wind noise band.

Furthermore, as illustrated in FIG. 5, a case where the road noise band is "small" and the wind noise band is "small" in accumulated vehicle interior sound frequency distribution $Fs_n$ in the last period (one period before) (graph 403 illustrated in FIG. 4) is associated with a candidate sound pressure change method to "raise" both of the sound pressures in the road noise band and the wind noise band or candidate sound pressure change methods to "raise" either of the sound pressures in the road noise band and the wind noise band.

In FIG. 5, where results of comparison between sound pressures in the respective particular frequency bands of accumulated vehicle interior sound and sound pressures in the reference frequency distribution in a period one period before are all "large" (graph 400 in FIG. 4), the sound pressures in each of the particular frequency bands are not changed.

In other words, as illustrated in FIG. 5, sound pressure change setting section 105 determines a sound pressure change method for each of the particular frequency bands according to records of magnitude relationships between the sound pressures in the respective particular frequency bands of the vehicle interior sound and the respective thresholds (sound pressures in the respective particular frequency bands of the reference sound) (here, magnitude relationship records of a period one period before a current time). Specifically, as illustrated in FIG. 5, the magnitude relationship records are indicated by magnitude relationship patterns for each predetermined period of time (here, a period separated by trigger signals), and setting section 1052 in sound pressure change setting section 105 sets a sound pressure change for each particular frequency band based on the association relationships in which the candidate magnitude relationship patterns (four candidate patterns in FIG. 5) are associated with respective candidate sound pressure change methods.

In the association relationships, as illustrated in FIG. 5, a pattern in which a sound pressure in a particular frequency band is smaller than a threshold (sound pressure of reference sound) in a period one period before (period one period before a current time) is associated with a candidate sound pressure change method that increases the sound pressure in the particular frequency band.

As described above, wakefulness-maintaining apparatus 100 reproduces control sound obtained by raising a sound pressure in a particular frequency band in an accumulated vehicle interior sound frequency distribution that is smaller than a sound pressure in a reference frequency distribution in a period one period before. Here, the amount of sound pressure change that can be perceived by a driver is larger in a case where a sound pressure that is smaller than a sound pressure in a reference frequency distribution is raised compared with a case where a sound pressure that is equal or larger than a sound pressure in a reference frequency distribution is raised. In other words, a change in sound characteristics (here, a sound pressure difference) can be perceived better by a driver in a case where a sound pressure in a frequency band that is originally small (smaller than a sound pressure in the reference frequency distribution) is raised, compared with a case where a sound pressure in a frequency band that is originally large (equal to or larger than a sound pressure in the reference frequency distribution) is raised.

Accordingly, wakefulness-maintaining apparatus 100 raises a sound pressure in a particular frequency band that is smaller in sound heard by a driver (accumulated vehicle interior sound), reliably allowing the driver to hear sound with characteristics largely changed, enabling maintenance of wakefulness of the driver.

Figure 6:
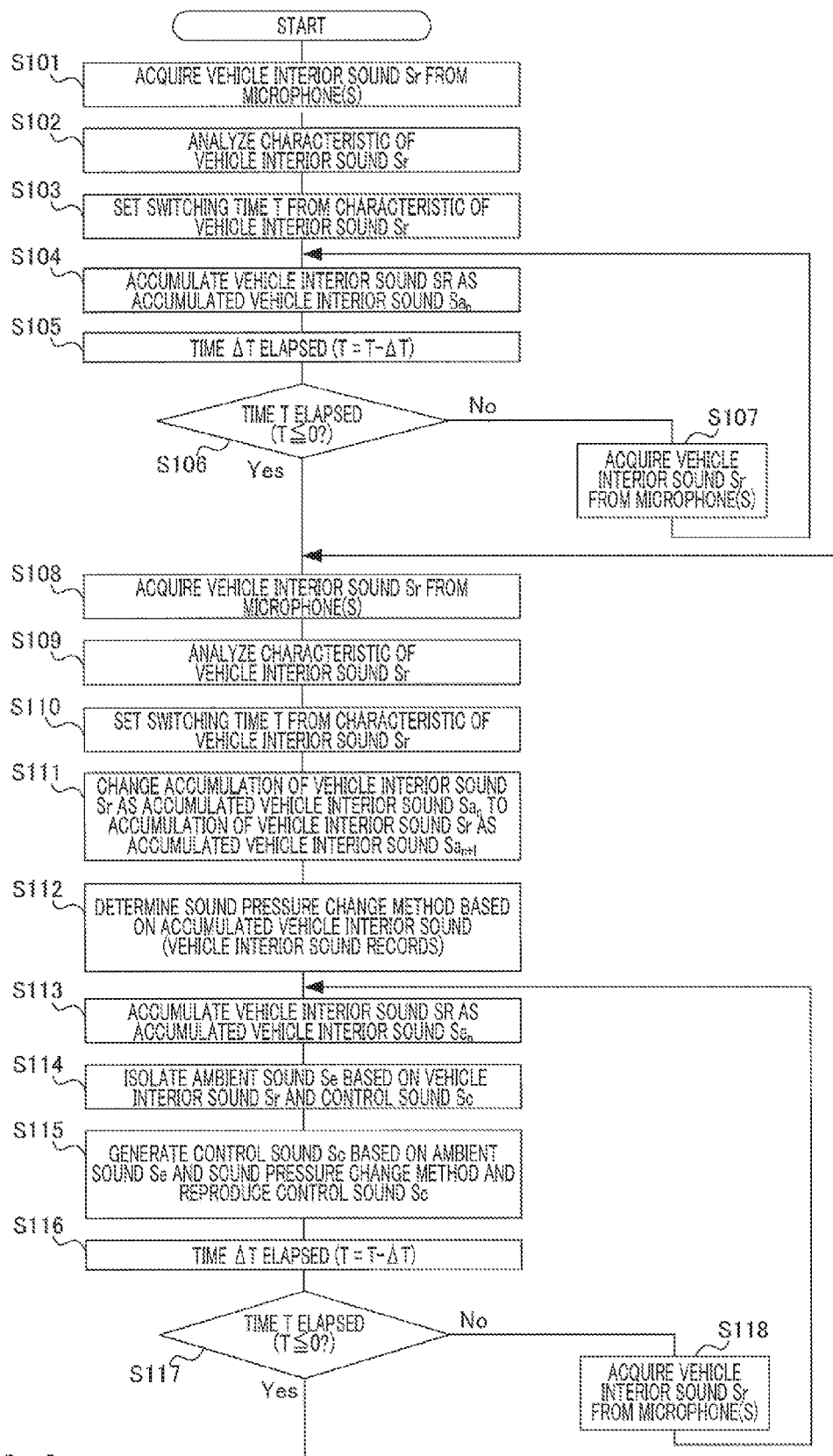
FIG. 6 is a flowchart provided for description of operation of a wakefulness-maintaining apparatus according to Embodiment 1 of the present invention.

Next, the flow of processing in wakefulness-maintaining apparatus 100 will be described. FIG. 6 is a flowchart provided for description of operation of wakefulness-maintaining apparatus 100.

In step S101, vehicle interior sound acquiring section 101 acquires vehicle interior sound Sr using, for example, the microphone(s).

In step S102, switching time control section 102 analyzes a characteristic of vehicle interior sound Sr, and in step S103, switching time control section 102 sets switching time T from the characteristic of vehicle interior sound Sr.

In step S104, vehicle interior sound accumulating section 103 accumulates vehicle interior sound Sr acquired in step S101 as accumulated vehicle interior sound $Sa_n$.

In step S105, switching time control section 102 calculates updated switching time T $(=T-\Delta T)$ by subtracting a predetermined period of time (time elapsed from the start of timer) $\Delta T$ from switching time T held at a current time (value set in step S103).

In step S106, switching time control section 102 determines whether or not switching time T updated in step S105 is equal to or smaller than zero. If updated switching time T is not equal to or smaller than zero (NO in step S106), in step S107, vehicle interior sound acquiring section 101 acquires vehicle interior sound Sr and the processing returns to step S104. The processing in step S107 and the processing from step S104 to step S106 are repeated until it is determined that updated switching time is equal to or smaller than zero.

If it is determined that updated switching time T is equal to or smaller than zero (YES in step S106), in step S108, vehicle interior sound acquiring section 101 acquires vehicle interior sound Sr, in step S109, switching time control section 102 analyzes a characteristic of vehicle interior sound Sr, and in step S110, switching time control section 102 sets new switching time T based on the characteristic of vehicle interior sound Sr. In step S111, vehicle interior sound accumulating section 103 switches accumulation of vehicle interior sound Sr from accumulation as accumulated vehicle interior sound $Sa_n$ to accumulation as accumulated vehicle interior sound $Sa_{n+1}$ for a next period (that is, n=n+1).

In step S112, sound pressure change setting section 105 determines a sound pressure change method used for generating next control sound Sc, based on accumulated vehicle interior sound (vehicle interior sound records) $Sa_n$. For example, comparison section 1051 in sound pressure change setting section 105 determines a magnitude relationship between a sound pressure in a particular frequency band in accumulated vehicle interior sound frequency distribution $Fs_n$ and a sound pressure in a frequency band corresponding to the particular frequency band in reference frequency distribution Fb each predetermined period of time corresponding to switching time T. Then, setting section 1052 in sound pressure change setting section 105 determines a sound pressure change method according to, for example, the association relationships illustrated in FIG. 5.

In step S113, vehicle interior sound accumulating section 103 accumulates vehicle interior sound Sr acquired in step S108 as accumulated vehicle interior sound $Sa_n$.

In step S114, ambient sound isolating section 104 isolates ambient sound Se based on vehicle interior sound Sr acquired in step S108 and control sound Sc. Here, where control sound Sc does not exist, ambient sound isolating section 104 regards vehicle interior sound Sr as ambient sound Se.

In step S115, control sound generating section 106 generates control sound Sc by applying the sound pressure change method determined in step S112 to ambient sound Se obtained in step S114, and control sound reproducing section 107 reproduces generated control sound Sc.

In step S116, switching time control section 102 calculates updated switching time T $(=T-\Delta T)$ by subtracting a predetermined period of time (time elapsed from the start of timer) ΔT from switching time T held at the current time (value set in step S110).

In step S117, switching time control section 102 determines whether or not switching time T updated in step S116 is equal to or smaller than zero. If updated switching time T is not equal to or smaller than zero (NO in step S117), in step S118, vehicle interior sound acquiring section 101 acquires vehicle interior sound Sr, and the processing returns to step S113. The processing in step S118 and the processing in step S113 to step S117 are repeated until it is determined that updated switching time T is equal to or smaller than zero.

If it is determined that updated switching time T is equal to or smaller than zero (YES in step S117), the processing from step S108 is performed again.

As described above, according to the present embodiment, in wakefulness-maintaining apparatus 100, vehicle interior sound accumulating section 103 accumulates vehicle interior sound resulting from combination of control sound reproduced by wakefulness-maintaining apparatus 100 and ambient sound around a driver in a state in which no control sound is reproduced, comparison section 1051 in sound pressure change setting section 105 compares sound pressures in two or more particular frequency bands in the accumulated vehicle interior sound with respective thresholds that are set in advance to determine magnitude relationships between the sound pressures in the respective particular frequency bands and the respective thresholds, setting section 1052 in sound pressure change setting section 105 sets a sound pressure change for each particular frequency band according to a record of the magnitude relationship in the particular frequency band, control sound generating section 106 generates control sound by applying the sound pressure change that is set by setting section 1052 to the ambient sound, time setting section 1021 sets switching time T based on a result of analysis of a characteristic of the vehicle interior sound, and time control section 1022 sets a timing for setting a sound pressure change method to be applied to ambient sound Se.

Consequently, it is possible to reliably allow a driver to hear vehicle interior sound whose sound pressure has been changed according to a record of vehicle interior sound the driver heard in the past (here, a record of a magnitude relationship between the vehicle interior sound and a threshold), in each particular period of time (each time switching time T has elapsed). Specifically, a driver can hear vehicle interior sound in which a sound pressure whose sound pressure change can easily be perceived (sound pressure in a frequency band in an accumulated vehicle interior sound frequency distribution that is smaller than a sound pressure in the reference frequency distribution) has been changed (raised). Therefore, according to the present embodiment, wakefulness of a driver can be maintained by reliably making the driver perceive a change in sound characteristics.

In the present embodiment, a case has been described in FIG. 5 where if sound pressures in all of particular frequency bands in accumulated vehicle interior sound frequency distribution $Fs_n$ are equal to or larger than corresponding sound pressures in reference frequency distribution Fb, none of the sound pressures are changed. However, a candidate sound pressure change method to attenuate a sound pressure in at least one frequency band from among the particular frequency bands may be associated with a case where sound pressures in all of particular frequency bands in accumulated vehicle interior sound frequency distribution $Fs_n$ are equal to or larger than corresponding sound pressures in reference frequency distribution Fb. For example, a sound pressure change method in which sound pressure change(s) of both or either of the road noise band and the wind noise band is (are) "attenuation" may be associated with a case where records of accumulated vehicle interior sound in a period one period before are (the road noise band is "large" and the wind noise band is "large"). In other words, in this case, for a sound pressure in a frequency band in accumulated vehicle interior sound frequency distribution $Fs_n$ that is smaller than a sound pressure in reference frequency distribution Fb, a sound pressure change method to raise or not change the sound pressure is applied, and for a sound pressure in a frequency band in accumulated vehicle interior sound frequency distribution $Fs_n$ that is equal to or larger than a sound pressure in reference frequency distribution Fb, a sound pressure change method to attenuate or not change the sound pressure is applied. In this case, also, wakefulness-maintaining apparatus 100 enables a driver to perceive the sound pressure change (sound pressure attenuation) between the vehicle interior sound the driver heard previously and the vehicle interior sound the driver heard at the present time.

Also, in the present embodiment, wakefulness-maintaining apparatus 100 may, for example, hold a table indicating the association relationships illustrated in FIG. 5, and determine a sound pressure change method based on magnitude relationships between sound pressures of accumulated vehicle interior sound in a period one period before and respective thresholds (sound pressures of reference sound), and the table.

[Embodiment 2]

While in Embodiment 1, a case where only accumulated vehicle interior sound in a period one period before (one period before a current time) is used has been described, in the present embodiment, a case where accumulated vehicle interior sound in a period two periods before (two periods before a current time) is used will be described.

Figure 7:
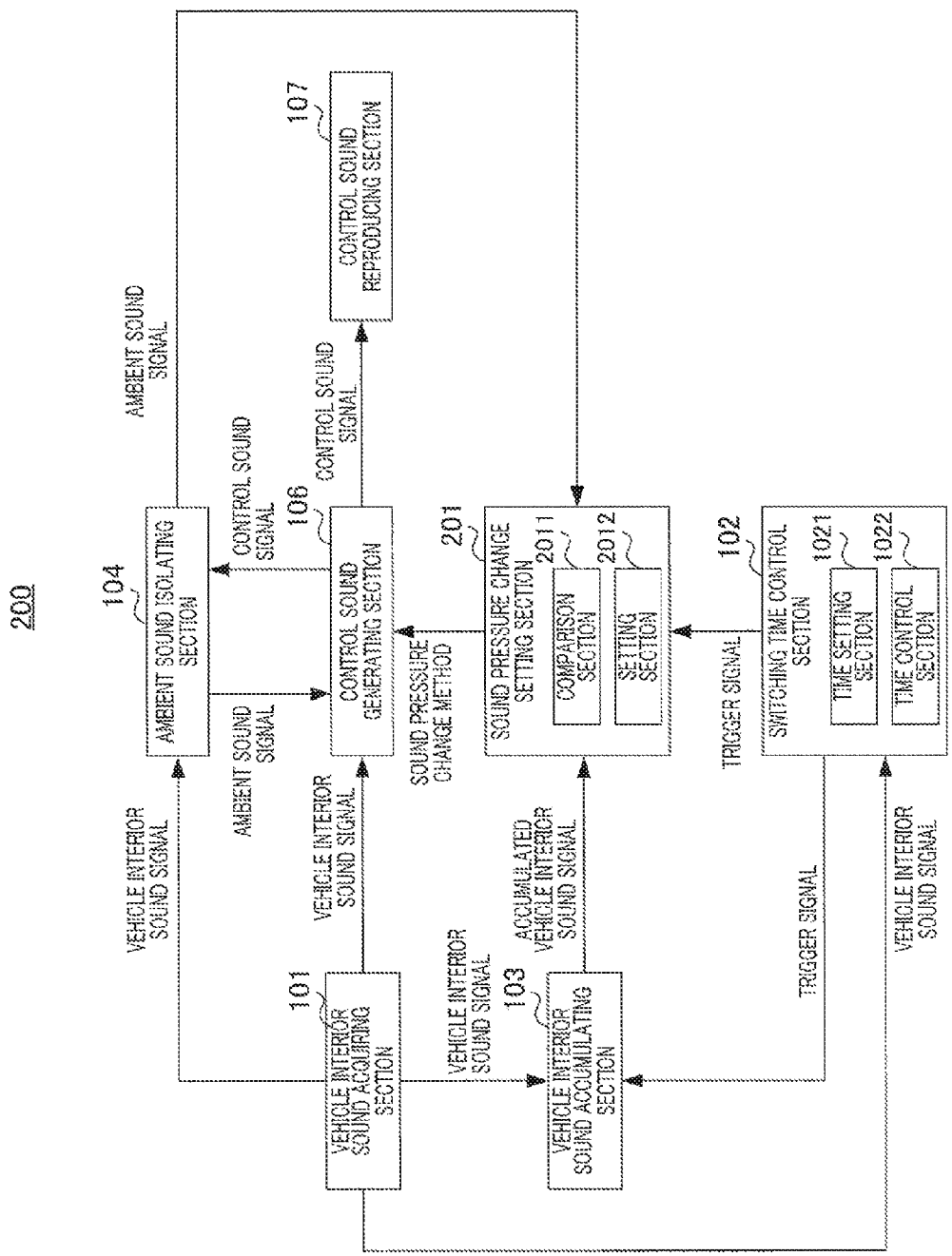
FIG. 7 is a block diagram illustrating a configuration of a wakefulness-maintaining apparatus according to Embodiment 2 of the present invention.

FIG. 7 is a block diagram illustrating a configuration of wakefulness-maintaining apparatus 200 according to the present embodiment. In FIG. 7, wakefulness-maintaining apparatus 200 is different from wakefulness-maintaining apparatus 100 (FIG. 1) in that processing in sound pressure change setting section 201 is different from that in sound pressure change setting section 105 in Embodiment 1.

In FIG. 7, upon reception of a trigger signal from switching time control section 102, sound pressure change setting section 201 acquires accumulated vehicle interior sound $Sa_n$ accumulated in vehicle interior sound accumulating section 103 from reception of a previous trigger signal (in a period one period before) until the reception of the trigger signal at the present time, and accumulated vehicle interior sounds $Sa_{n-1}$ accumulated in vehicle interior sound accumulating section 103 from reception of a second previous trigger signal (in a period two periods before) until the reception of the previous trigger signal (in the period one period before), and acquires ambient sound Se from ambient sound isolating section 104. Then, sound pressure change setting section 201 sets a sound pressure change method to be applied when generating next control sound Sc, based on accumulated vehicle interior sound $Sa_n$, accumulated vehicle interior sound $Sa_{n-1}$ and ambient sound Se.

Specifically, sound pressure change setting section 201 calculates frequency distribution (accumulated vehicle interior sound frequency distribution) $Fs_n$ of acquired accumulated vehicle interior sound $Sa_n$, and also calculates frequency distribution (accumulated vehicle interior sound frequency distribution) $Fs_{n-1}$ of accumulated vehicle interior sound $Sa_{n-1}$, and calculates frequency distribution (ambient sound frequency distribution) Fe of ambient sound Se. Comparison section 2011 in sound pressure change setting section 201 compares sound pressures in at least two particular frequency bands in accumulated vehicle interior sound frequency distribution $Fs_n$ with sound pressures in frequency bands in reference frequency distribution Fb that correspond to the particular frequency bands (thresholds) to determine magnitude relationships between the sound pressures in the respective particular frequency bands and the respective thresholds in the period one period before. Then, as in Embodiment 1, if, as a result of the comparison in comparison section 2011, there is at least one particular frequency band (first frequency band) in which the sound pressure of accumulated vehicle interior sound frequency distribution $Fs_n$ is smaller than the corresponding sound pressure in reference frequency distribution Fb, setting section 2012 in sound pressure change setting section 201 sets a candidate sound pressure change method to raise the sound pressure in the at least one frequency band from among the particular frequency bands.

Subsequently, sound pressure change setting section 201 sets a sound pressure change method for a particular frequency band in accumulated vehicle interior sound frequency distribution $Fs_n$ whose sound pressure is equal to or larger than the corresponding sound pressure in reference frequency distribution Fb. For example, sound pressure change setting section 201 applies the candidate sound pressure change method to be set for the first frequency band to ambient sound Se to calculate candidate sound frequency distribution Fc. Comparison section 2011 in sound pressure change setting section 201 makes comparison on a sound pressure magnitude relationship in the second frequency band between calculated candidate sound frequency distribution Fc and reference frequency distribution Fb, and makes comparison on a sound pressure magnitude relationship in the second frequency band between accumulated vehicle interior sound frequency distribution $Fs_{n-1}$ in the period before the last one and reference frequency distribution Fb. Then, if the sound pressure magnitude relationship with the sound pressure in reference frequency distribution Fb is the same between candidate sound frequency distribution Fc and accumulated vehicle interior sound frequency distribution $Fs_{n-1}$, sound pressure change setting section 201 sets a candidate sound pressure change for attenuating the sound pressure in the second frequency band, and if the magnitude relationship with the sound pressure in reference frequency distribution Fb is different between the same, sound pressure change setting section 201 sets a candidate sound pressure change for not changing the sound pressure in the second frequency band.

In other words, for a particular frequency band (first frequency band) whose sound pressure in accumulated vehicle interior sound frequency distribution $Fs_n$ is smaller than a corresponding sound pressure in reference frequency distribution Fb, as in Embodiment 1, sound pressure change setting section 201 raises the sound pressure. Furthermore, for a particular frequency band (second frequency band) whose sound pressure in accumulated vehicle interior sound frequency distribution $Fs_n$ is equal to or larger than the corresponding sound pressure in reference frequency distribution Fb, sound pressure change setting section 201 changes the sound pressure (attenuates the sound pressure or does not change the sound pressure) so that the sound pressure is different from the sound pressure in accumulated vehicle interior sound frequency distribution $Fs_{n-1}$. In other words, sound pressure change setting section 201 sets a sound pressure change method so that the frequency distribution after the sound pressure change and accumulated vehicle interior sound frequency distribution $Fs_{n-1}$ in the period before the last one are different from each other.

Next, processing for setting a sound pressure change method in sound pressure change setting section 201 will be described.

Here, as in Embodiment 1, candidate sound pressure change methods where particular frequency bands in an accumulated vehicle interior sound frequency distribution are two bands that are a road noise band and a wind noise band are indicated.

Also, as in Embodiment 1, in the particular frequency bands (the road noise band and the wind noise band), "large" represents a case where a sound pressure in an accumulated vehicle interior sound frequency distribution is equal to or larger than a sound pressure in a reference frequency distribution, and "small" represents a case where a sound to pressure in an accumulated vehicle interior sound frequency distribution is smaller than a sound pressure in the reference frequency distribution. Also, "raising" represents a case where the sound pressure is increased when generating next control sound Sc, "attenuation" represents a case where the sound pressure is decreased, and "-" represents a case where the sound pressure is not changed. No sound pressure change methods are associated with sound pressure record patterns that cannot occur.

Figure 8:
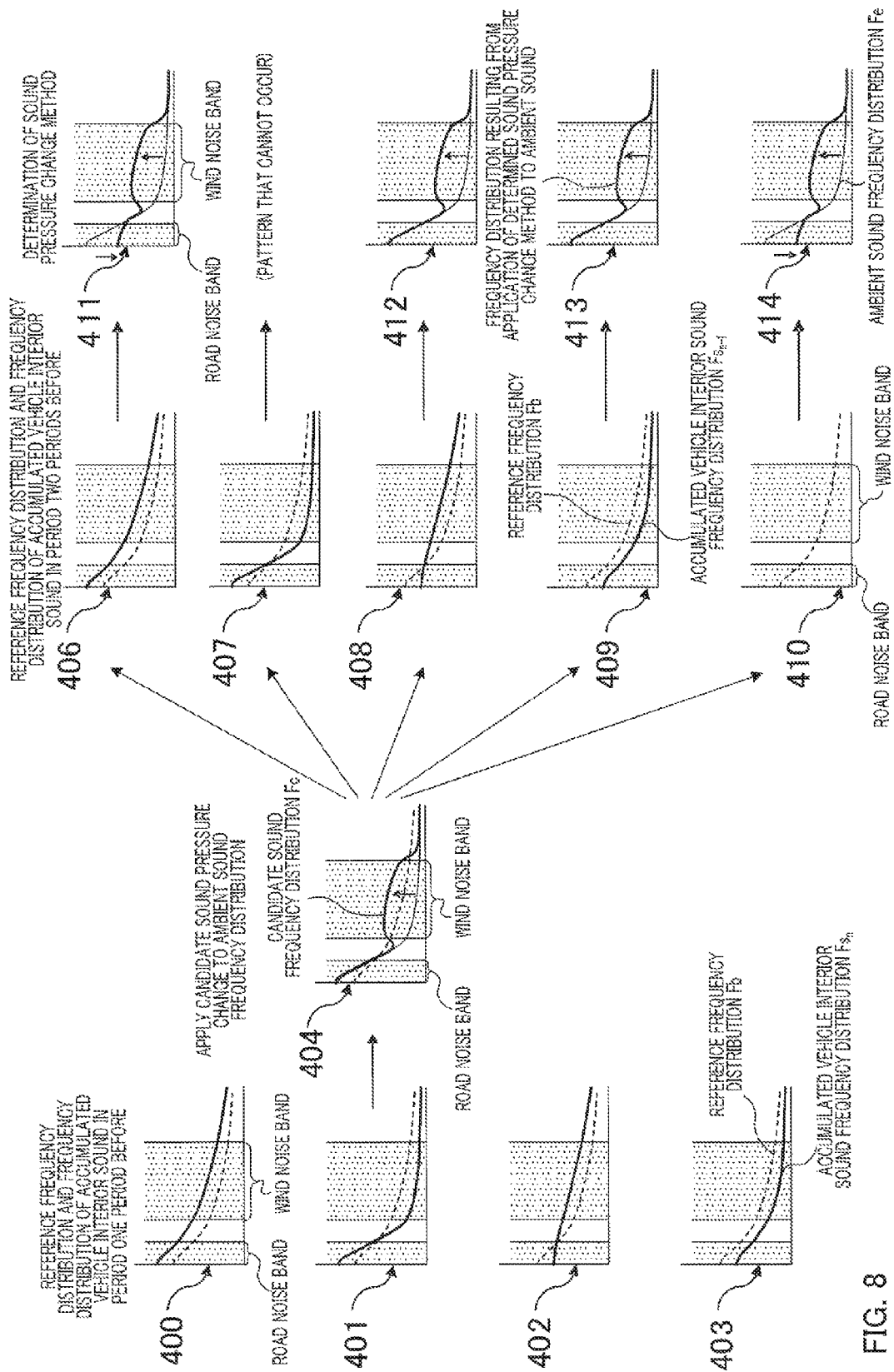
FIG. 8 is a diagram provided for description of processing in a sound pressure change setting section according to Embodiment 2 of the present invention.

FIG. 8 illustrates an example of processing for setting a sound pressure change method in sound pressure change setting section 201. In FIG. 8, the abscissa axis represents frequency and the ordinate axis represents sound pressure level.

Comparison section 2011 in sound pressure change setting section 201 compares sound pressures in the road noise band and the wind noise band in accumulated vehicle interior sound frequency distribution $Fs_n$ with sound pressures in the road noise band and the wind noise band in reference frequency distribution Fb, respectively. For example, in graph 401 illustrated in FIG. 8, in accumulated vehicle interior sound frequency distribution $Fs_n$ in the last period (period one period before a current time), the road noise band is "large" and the wind noise band is "small."

Therefore, setting section 2012 in sound pressure change setting section 201 sets a sound pressure change method to raise a sound pressure in the wind noise band (first frequency band) in which the sound pressure of accumulated vehicle interior sound frequency distribution $Fs_n$ is smaller than the sound pressure in reference frequency distribution Fb. In other words, setting section 2012 raises the sound pressure in the wind noise band that is smaller than the sound pressure in reference frequency distribution Fb irrespective of accumulated vehicle interior sound frequency distribution $Fs_{n-1}$ in the period before the last one (period two periods before the current time). Consequently, as indicated in graph 404 in FIG. 8, candidate sound frequency distribution Fc in which a sound pressure in the wind noise band of ambient sound Se has been changed.

Subsequently, setting section 2012 sets a sound pressure in the road noise band (second frequency band) in which the sound pressure of accumulated vehicle interior sound frequency distribution $Fs_n$ is equal to or larger than a sound pressure in reference frequency distribution Fb. Specifically, setting section 2012 determines a sound pressure change so that accumulated vehicle interior sound frequency distribution $Fs_{n-1}$ in the period before the last one (two periods before the current time) and candidate sound frequency distribution Fc are different from each other in the road noise band. In other words, setting section 2012 sets a sound pressure change for the road noise band (second frequency band) so that at least either the magnitude relationship with the threshold in the wind noise band (first frequency band) or the magnitude relationship with the threshold in the road noise band (second frequency band) is different between the accumulated vehicle interior sound in the period before the last one (two periods before) and candidate sound (vehicle interior sound candidate to be obtained by applying the sound pressure change for the wind noise band (first frequency band) set based on the magnitude relationship in the period one period before to ambient sound).

Graphs 406 to 410 illustrated in FIG. 8 each indicate a relationship between accumulated vehicle interior sound frequency distribution $Fs_{n-1}$ that can occur in the period before the last one (two periods before) and reference frequency distribution Fb.

For example, a case where accumulated vehicle interior sound frequency distribution $Fs_{n-1}$ in the period before the last one (two periods before) is one indicated in graph 406 (the road noise band is "large" and the wind noise band is "large") in FIG. 8 will be described.

The road noise band is "large" in graph 404 and the road noise band is "large" in graph 406. In other words, the magnitude relationship with the sound pressure (threshold) in reference frequency distribution Fb is the same between graphs 404 and 406.

Here, for example, where accumulated vehicle interior sound frequency distribution $Fs_n$ is one indicated in graph 401 and accumulated vehicle interior sound frequency distribution $Fs_{n-1}$ is one indicated in graph 406, if a sound pressure in the road noise band is not changed, in vehicle interior sound frequency distribution ($Fs_{n+1}$) for a next period, the road noise band is "large" and the wind noise band is "large". In other words, such case results in a frequency distribution in which vehicle interior sound frequency distribution ($Fs_{n+1}$) for the next period and vehicle interior sound frequency distribution ($Fs_{n-1}$) in the period before the last one are similar to each other. In other words, vehicle interior sound frequency distribution ($Fs_{n+1}$) for the next period is a return to graph 406, which indicates vehicle interior sound frequency distribution ($Fs_{n-1}$) in the period before the last one, resulting in a monotonous sound pressure change.

Meanwhile, as described above, where accumulated vehicle interior sound frequency distribution $Fs_n$ is one indicated in graph 401 and accumulated vehicle interior sound frequency distribution $Fs_{n-1}$ is one indicated in graph 406, if a sound pressure in the road noise band is attenuated, in vehicle interior sound frequency distribution ($Fs_{n+1}$) for the next period, the road noise band is "small" and the wind noise band is "large" (graph 411). In other words, such case results in a frequency distribution in which vehicle interior sound frequency distribution ($Fs_{n+1}$) for the next period and vehicle interior sound frequency distribution ($Fs_{n-1}$) in the period before the last one are different from each other. In other words, vehicle interior sound frequency distribution ($Fs_{n+1}$) for the next period is different from graph 406, which indicates vehicle interior sound frequency distribution ($Fs_{n-1}$) in the period before the last one, and thus, sound pressure changes providing patterns different from one another through a plurality of periods can be provided.

Therefore, setting section 2012 sets a candidate sound pressure change to attenuate the sound pressure in the road noise band. In other words, where accumulated vehicle interior sound frequency distribution $Fs_n$ in the last period (one period before) is one indicated in graph 401 (the road noise band is "large" and the wind noise band is "small") and accumulated vehicle interior sound frequency distribution $Fs_{n-1}$ in the period before the last one (two periods before) is one indicated in graph 406 (the road noise band is "large" and the wind noise band is "large"), setting section 2012 sets a sound pressure change method (411) to attenuate the sound pressure in the road noise band and raise the sound pressure in the wind noise band.

Likewise, for example, a case will be described where accumulated vehicle interior sound frequency distribution $Fs_{n-1}$ in the period before the last one (two periods before) is one indicated in graph 408 (the road noise band is "small" and the wind noise band is "large") in FIG. 8.

The road noise band in graph 404 is "large" and the road noise band in graph 408 is "small". In other words, the magnitude relationship with the sound pressure (threshold) in reference frequency distribution Fb is different between graphs 404 and 408.

Here, for example, where accumulated vehicle interior sound frequency distribution $Fs_n$ is one indicated in graph 401 and accumulated vehicle interior sound frequency distribution $Fs_{n-1}$ is one indicated in graph 408, if the sound pressure in the road noise band is attenuated, in vehicle interior sound frequency distribution ($Fs_{n+1}$) for the next period, the road noise band is "small" and the wind noise band is "large." In other words, such case results in a frequency distribution in which vehicle interior sound frequency distribution ($Fs_{n+1}$) for the next period and vehicle interior sound frequency distribution ($Fs_{n-1}$) for the period before the last one are similar to each other. Meanwhile, where accumulated vehicle interior sound frequency distribution $Fs_n$ is one indicated in graph 401 and accumulated vehicle interior sound frequency distribution $Fs_{n-1}$ is one indicated in graph 408, if the sound pressure in the road noise band is not changed, in vehicle interior sound frequency distribution ($Fs_{n+1}$) for the next period, the road noise band is "large" and the wind noise band is "large" (412). In other words, such case results in a frequency distribution in which vehicle interior sound frequency distribution ($Fs_{n+1}$) for the next period and vehicle interior sound frequency distribution ($Fs_{n-1}$) in the second previous period are different from each other.

Therefore, setting section 2012 sets a candidate sound pressure change that does not change the sound pressure in the road noise band. In other words, where accumulated vehicle interior sound frequency distribution $Fs_n$ in the last period (one period before) is one indicated in graph 401 (the road noise band is "large" and the wind noise band is "small") and accumulated vehicle interior sound frequency distribution $Fs_{n-1}$ in the period before the last one (two periods before) is one indicated in graph 408 (the road noise band is "small" and the wind noise band is "large"), setting section 2012 sets sound pressure change method (412) to raise the sound pressure in the wind noise band without changing the sound pressure in the road noise band.

In a case where accumulated vehicle interior sound frequency distribution $Fs_n$ is one indicated in graph 401 illustrated in FIG. 8, also, a case where accumulated vehicle interior sound frequency distribution $Fs_{n-1}$ exhibits another pattern (409 or 410) is associated with a sound pressure change method (413 or 414), in a manner similar to that described above.

Here, since it is assumed that no case where distributions in graphs 401 and 407 illustrated in FIG. 8 are generated, that is, no case where a previous accumulated vehicle interior sound frequency distribution and a second previous accumulated vehicle interior sound frequency distribution have a same magnitude relationship with the reference frequency distribution can occur, no candidate sound pressure change method is associated with such case. Also, in graph 410 illustrated in FIG. 8 (where there is no accumulated vehicle interior sound in the period two periods before), setting section 2012 sets a sound pressure change method so that the magnitude relationships with the thresholds in the road noise band and the wind noise band are different between the accumulated sound one period before and ambient sound after sound pressure change application.

As in graph 401, also for each of cases where accumulated vehicle interior sound frequency distribution $Fs_n$ are ones indicated in graphs 400, 402 and 403 in FIG. 8, a sound pressure change method is set.

As described above, in sound pressure change setting section 201, comparison section 2011 determines a magnitude relationship between the sound pressure in each of the particular frequency bands and a corresponding one of the thresholds (sound pressure of the reference sound) in a period one period before a current time and a period two periods before the current time. Then, setting section 2012 increases a sound pressure in a frequency band (first frequency band) that is smaller than the corresponding threshold in the period one period before the current time from among the particular frequency bands, and changes a sound pressure in a frequency band (second frequency band) that is equal to or larger than the corresponding threshold in the period one period before the current time based on a sound pressure of vehicle interior sound in a period two or more periods before the current time (here, only the period two periods before). In such case, setting section 2012 does not change the sound pressure of the second frequency band that is smaller than the corresponding threshold (sound pressure of reference sound) in the period two periods before the current time (for example, graphs 412 or 413 illustrated in FIG. 8) and decreases the sound pressure in the second frequency band that is equal to or larger than the corresponding threshold in the period two periods before the current time (for example, graph 411 illustrated in FIG. 8).

FIG. 9 is a table indicating a summary of association relationships between magnitude relationships ("large" or "small") in the road noise band and the wind noise band between each of accumulated vehicle interior sound frequency distribution $Fs_n$ in the last period (one period before) and accumulated vehicle interior sound frequency distribution $Fs_{n-1}$ in the period before the last one (two periods before) and reference frequency distribution Fb (thresholds), and candidate sound pressure change methods.

For example, as illustrated in FIG. 9, a case where the road noise band is "large" and the wind noise band is "small" in accumulated vehicle interior sound frequency distribution $Fs_n$ in the last period (one time before) (graph 401 illustrated in FIG. 8) will be described.

In this case, a case where the road noise band is "large" and the wind noise band is "large" in accumulated vehicle interior sound frequency distribution $Fs_{n-1}$ in the period before the last one (two periods before) (graph 406 illustrated in FIG. 8) is associated with a candidate sound pressure change method to "attenuate" a sound pressure in the road noise band and "raise" a sound pressure in the wind noise band (graph 411 in FIG. 8). Likewise, a case where the road noise band is "small" and the wind noise band is "large" in accumulated vehicle interior sound frequency distribution $Fs_{n-1}$ in the period before the last one (two periods before) (graph 408 illustrated in FIG. 8) is associated with a candidate sound pressure change method to "raise" a sound pressure in the wind noise band without changing a sound pressure in the road noise band (graph 412 illustrated in FIG. 8). Furthermore, a case where the road noise band is "small" and the wind noise band is "small" in accumulated vehicle interior sound frequency distribution $Fs_{n-1}$ in the period before the last one (two periods before) (graph 409 illustrated in FIG. 8) is associated with a candidate sound pressure change method to "raise" a sound pressure in the wind noise band without changing a sound pressure of the road noise band (graph 413 illustrated in FIG. 8). Also, a case where there is no accumulated vehicle interior sound frequency distribution $Fs_{n-1}$ in the period before the last one (two periods before) (graph 410 illustrated in FIG. 8) is associated with a candidate sound pressure change method to attenuate a sound pressure in the road noise band and "raise" a sound pressure in the wind noise band (graph 414 illustrated in FIG. 8). Here, no candidate sound pressure change method is associated with a case where the road noise band is "large" and the wind noise band is "small" in accumulated vehicle interior sound frequency distribution $Fs_{n-1}$ in the period before the last one (two periods before) (graph 407 in FIG. 8), that is, a case where accumulated vehicle interior sound frequency distribution $Fs_{n-1}$ in each of the road noise band and the wind noise band is the same as accumulated vehicle interior sound frequency distribution $Fs_n$ in the last period (one period before).

In FIG. 9, record patterns other than the aforementioned record patterns are also associated with candidate sound pressure change methods.

In other words, as illustrated in FIG. 9, sound pressure change setting section 201 determines a sound pressure change method for each of the particular frequency bands according to records of the magnitude relationships between sound pressures in the respective particular frequency bands in the vehicle interior sound and the respective thresholds (sound pressures in the respective particular frequency bands of reference sound) (here, records of magnitude relationships for the period one period before the current time and the period two periods before the current time). Specifically, as illustrated in FIG. 9, the records of the magnitude relationships are indicated by magnitude relationship patterns for each predetermined period of time (here, a period separated by trigger signals), setting section 2012 in sound pressure change setting section 201 sets a sound pressure change for each of the particular frequency bands based on the association relationships between the candidate magnitude relationship patterns (20 candidate patterns in FIG. 9) and the candidate sound pressure change methods.

Here, in the association relationships illustrated in FIG. 9, attention will be focused on accumulated vehicle interior sound (records of vehicle interior sound) in the last period (one period before). As illustrated in FIG. 9, in the association relationships, as in Embodiment 1 (FIG. 5), a pattern in which a sound pressure in a particular frequency band in the period one period before (period one period before the current time) is smaller than the corresponding threshold (sound pressure of the reference sound) is associated with a candidate sound pressure change that increases the sound pressure in the particular frequency band. A pattern in which sound pressures in particular frequency band in the period one period before are smaller than corresponding sound pressures (thresholds) in a reference frequency distribution is associated with a candidate sound pressure change method to "raise" the sound pressure in at least one of the particular frequency bands.

Although setting section 2012 in sound pressure change setting section 201 sets a sound pressure change method to "raise" or "attenuate" a sound pressure in the road noise band and a sound pressure in the wind noise band, a sound pressure change method to "attenuate" or "raise" a sound pressure other than that in the road noise band and a sound pressure other than that in the wind noise band may be set.

Consequently, as in Embodiment 1, wakefulness-maintaining apparatus 200 raises a sound pressure in a particular frequency band that is smaller in sound heard by a driver (accumulated vehicle interior sound), reliably allowing the driver to hear sound with characteristics largely changed, enabling maintenance of wakefulness of the driver.

On the other hand, as illustrated in FIG. 9, in the above association relationships, a pattern in which in a particular frequency band whose sound pressure in the last period (period one period before the current time) is equal to or larger than a corresponding threshold (sound pressure of reference sound) from among two or more particular frequency bands, the sound pressure is smaller than the corresponding threshold in the period before the last one (period two periods before the current time) is associated with a candidate sound pressure change method that does not change the sound pressure in the particular frequency band, and a pattern in which the sound pressure in the period before the last one is equal to or larger than the threshold is associated with a candidate sound pressure change method that reduces the sound pressure in the particular frequency band. In other words, in FIG. 9, in a particular frequency band whose sound pressure in the accumulated vehicle interior sound frequency distribution in the last period (one period before) is equal to or larger than the sound pressure (threshold) in the reference frequency distribution, whether the sound pressure is attenuated or not changed is determined based on the magnitude of the sound pressure of the accumulated vehicle interior sound in the period before the last one (two periods before) (magnitude relationship with the threshold).

Consequently, as illustrated in FIG. 8, frequency distributions (411 to 414) after sound pressure change and corresponding accumulated vehicle interior sound frequency distributions (406 to 410) in the period before the last one are different from each other, respectively. Specifically, where the distributions 411 to 414 and distributions 406 to 410 illustrated in FIG. 8 are compared, respectively, distributions 411 to 414 and distributions 406 to 410 exhibit different magnitude relationships with the sound pressure in the reference frequency distribution in both or either of the road noise band and the wind noise band. In other words, wakefulness-maintaining apparatus 200 reproduces sound different from sound reproduced in the period before the last one, whereby sound in a same (or similar) frequency distribution (monotonous repetition of sound) can be prevented from being repeatedly reproduced when changing the sound pressure of the ambient sound in each period.

Figure 10:
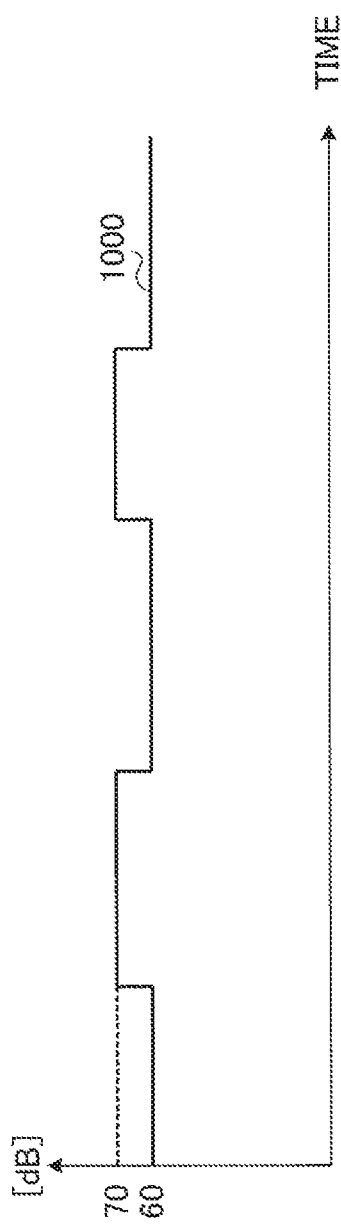
FIG. 10 is a diagram provided for description of sound pressure changes in a related art.
Figure 11:
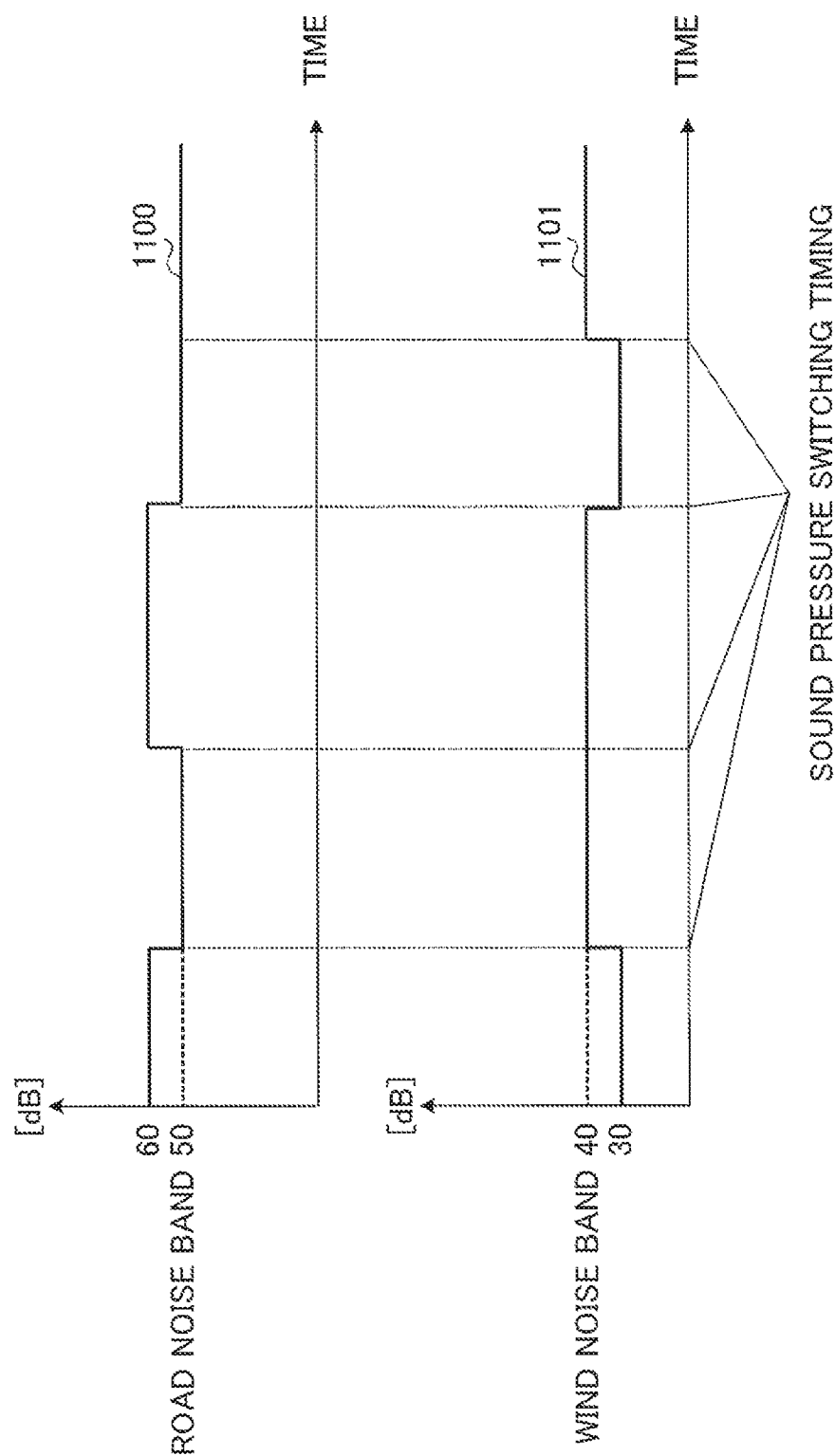
FIG. 11 is a diagram provided for description of sound pressure changes in Embodiment 2 of the present invention.

For example, in the related art (see, for example, Patent Literature 1), as illustrated n FIG. 10, senses of a driver can be stimulated by changing a sound pressure (1000 illustrated in FIG. 10) at regular intervals. However, a fixed amount of sound pressure change is monotonously repeated with passage of time, which may result in decrease in wakefulness if the driver hears sound for a long period of time. On the other hand, in the present embodiment, as illustrated in FIG. 11, when changing sound pressures in the particular frequency bands (1100 in the road noise band and 1101 in the wind noise band in FIG. 11) at a sound pressure switching timing (timing of the elapse of switching time T), sound having a characteristic that is at least different from that of sound reproduced in a period before the last one and the last period is reproduced. Consequently, sound in a same (or similar) frequency distribution is prevented from being repeatedly reproduced, enabling maintenance of wakefulness even if a driver hears the sound for a long period of time.

Figure 12:
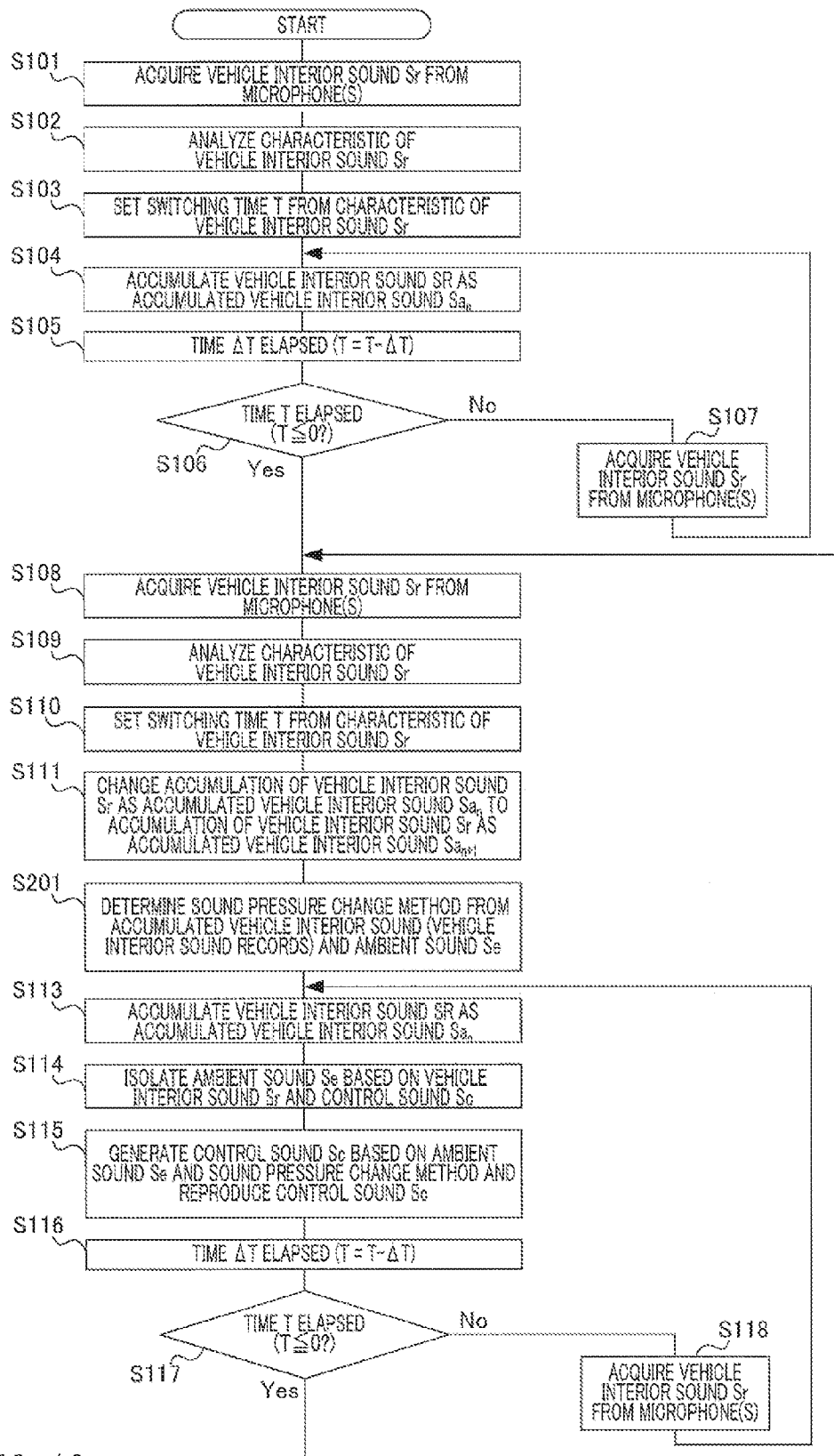
FIG. 12 is a flowchart provided for description of operation of the wakefulness-maintaining apparatus according to Embodiment 2 of the present invention.

Next, the flow of processing in wakefulness-maintaining apparatus 200 will be described. FIG. 12 is a flowchart provided for description of operation of wakefulness-maintaining apparatus 200. In FIG. 12, processing steps that are the same as those in Embodiment 1 (FIG. 6) are provided with reference numerals that are the same as those in Embodiment 1, and a description thereof will be omitted to avoid overlap.

In FIG. 12, in step S201, sound pressure change setting section 201 determines a sound pressure change method to be used for generating next control sound Sc, based on accumulated vehicle interior sound $Sa_n$, accumulated vehicle interior sound $Sa_{n-1}$ and ambient sound Se. For example, comparison section 2011 in sound pressure change setting section 201 determines magnitude relationships between sound pressures in the particular frequency bands of accumulated vehicle interior sound frequency distribution $Fs_n$ and accumulated vehicle interior sound frequency distribution $Fs_{n-1}$ and sound pressures in frequency bands corresponding to the particular frequency bands in reference frequency distribution Fb, in each one of predetermined periods separated by switching time T. Then, setting section 2012 in sound pressure change setting section 201 determines a sound pressure change method according to, for example, the association relationships illustrated in FIG. 9.

Consequently, as in Embodiment 1, a driver can hear vehicle interior sound whose sound pressure change that can easily be perceived (sound pressure in a frequency band in an accumulated vehicle interior sound frequency distribution that is smaller than a sound pressure in a reference frequency distribution) changed (raised). Further, prevention of monotonous sound pressure change patterns enables senses of a driver to be continuously stimulated even if the driver hears the sound for a long period of time. Consequently, according to the present embodiment, wakefulness of a driver can be maintained by reliably making the driver perceive changes in sound characteristics for a long period of time.

In the present embodiment, wakefulness-maintaining apparatus 200 may set a sound pressure change method according to a method other than the above-described method.

For example, if a sound pressure in a particular frequency band of accumulated vehicle interior sound frequency distribution $Fs_n$ is smaller than a corresponding sound pressure in reference frequency distribution Fb, as in the present embodiment, sound pressure change setting section 201 (FIG. 7) selects a candidate sound pressure change method that increases (raises) the sound pressure in the particular frequency band (first frequency band).

Subsequently, sound pressure change setting section 201 applies the candidate sound pressure change method selected for the first frequency band to ambient sound Se and also applies a sound pressure change method that may be set for a second frequency band (frequency band whose sound pressure in accumulated vehicle interior sound frequency distribution $Fs_n$ is equal to or larger than a corresponding sound pressure in reference frequency distribution Fb) (a method that attenuates the sound pressure or a method that does not change the sound pressure) to ambient sound Se, to calculate a plurality of candidate sound frequency distributions Fc. For example, with reference to FIG. 4, if accumulated vehicle interior sound frequency distribution $Fs_n$ is one indicated in graph 401, distributions indicated in graphs 404 and 405 are calculated as candidate sound frequency distributions Fc.

Next, sound pressure change setting section 201 determines magnitude relationships in sound pressures in the particular frequency bands between each of the calculated candidate sound frequency distributions Fc and reference frequency distribution (thresholds) Fb, and also determines magnitude relationships in sound pressures in the particular frequency bands between accumulated vehicle interior sound frequency distribution $Fs_{n-1}$ in a period before the last one and reference frequency distribution Fb. Then, sound pressure change setting section 201 determines a candidate sound pressure change method applied to candidate sound frequency distribution Fc including a largest number of parts whose magnitude relationships with the sound pressures in reference frequency distribution Fb are opposite to those in accumulated vehicle interior sound frequency distribution $Fs_{n-1}$, as a sound pressure change method to be used for generating next control sound Sc. Consequently, as in the present embodiment, a frequency distribution subsequent to application of the sound pressure change method and an accumulated vehicle interior sound frequency distribution in the period before the last one are made different from each other, enabling provision of effects similar to those of the present embodiment.

Also, in the present embodiment, wakefulness-maintaining apparatus 200 may, for example, hold a table indicating the association relationships illustrated in FIG. 9, and specify a sound pressure change method based on magnitude relationships between sound pressures of accumulated vehicle interior sound and corresponding thresholds (sound pressures of reference sound) in a period one period before and a period two periods before, and the table.

[Embodiment 3]

In the present embodiment, a case where ambient sound Se (for example, road noise or wind noise) varies will be described.

Figure 13:
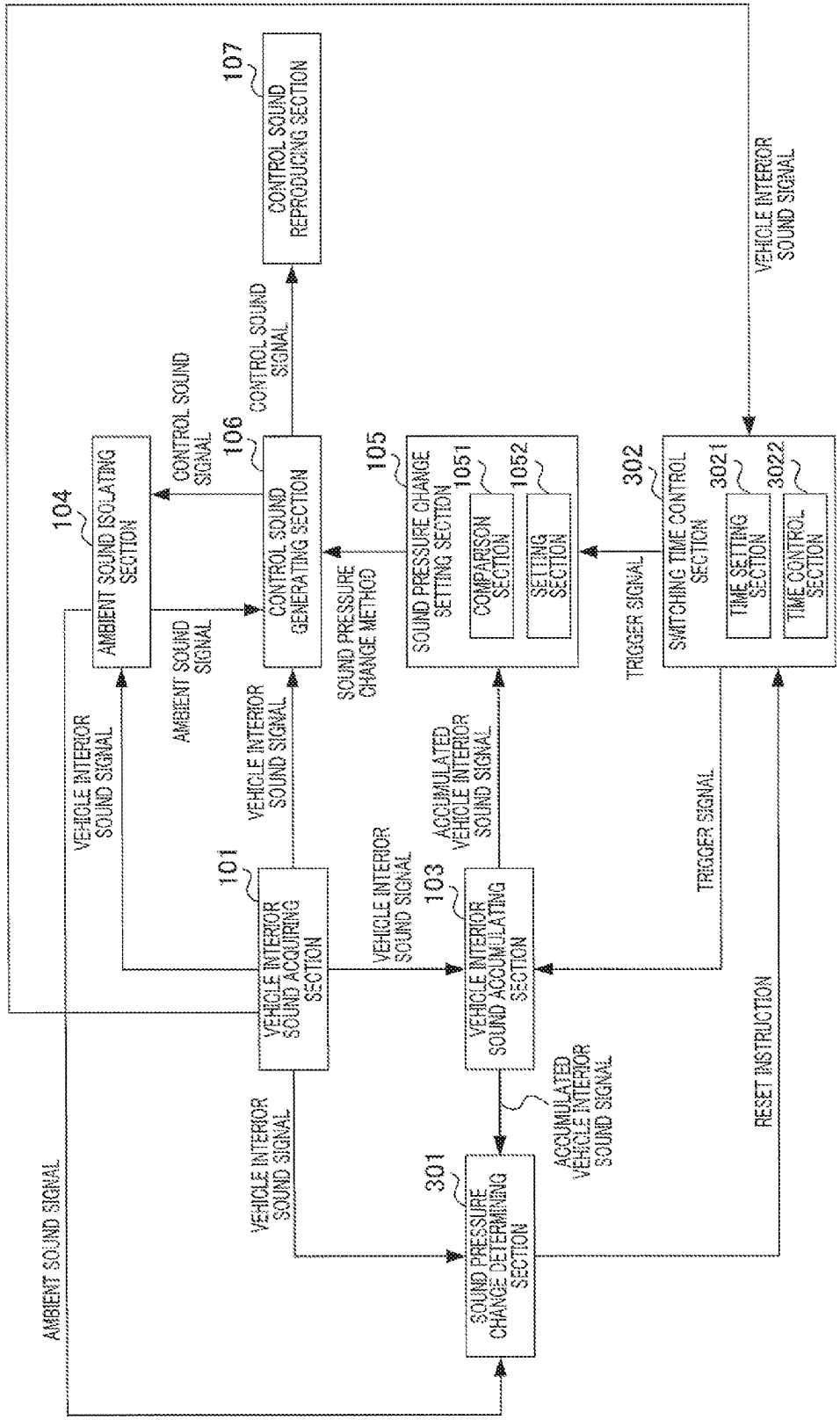
FIG. 13 is a block diagram illustrating a configuration of a wakefulness-maintaining apparatus according to Embodiment 3 of the present invention.

A description will be given below of parts different from those in Embodiment 1. FIG. 13 is a block diagram illustrating a configuration of wakefulness-maintaining apparatus 300 according to the present embodiment. In FIG. 13, in comparison with wakefulness-maintaining apparatus 100 (FIG. 1), in wakefulness-maintaining apparatus 300, sound pressure change determining section 301 is added, and processing in switching time control section 302 is different from that in switching time control section 102 in Embodiment 1.

In wakefulness-maintaining apparatus 300, sound pressure change determining section 301 compares vehicle interior sound Sr with accumulated vehicle interior sound $Sa_n$. Here, as described above, vehicle interior sound Sr acquired by vehicle interior sound acquiring section 101 is sound resulting from combination of control sound Sc and ambient sound Se. Accordingly, in vehicle interior sound Sr, sound pressure changes attributed to control sound Sc generated by wakefulness-maintaining apparatus 300 (sound pressure changes attributed to the system) and sound pressure changes not attributed to wakefulness-maintaining apparatus 300 occur. Examples of the sound pressure changes not attributed to wakefulness-maintaining apparatus 300 may include a change in ambient sound Se attributed to a change in environment of the outside of a vehicle (environment around a driver) (for example, a change in road surface on which the vehicle runs).

Subsequently, if sound pressure change determining section 301 determines that a sound pressure change where a sound pressure change method specified based on accumulated vehicle interior sound $Sa_n$ at a current time is applied to ambient sound and a change in vehicle interior sound Sr are equivalent to each other, sound pressure change determining section 301 outputs a reset instruction to switching time control section 1202. Here, the reset instruction refers to an instruction for making switching time control section 302 perform an operation that is the same as that performed when switching time T reaches zero or smaller.

Specifically, sound pressure change determining section 301 acquires vehicle interior sound Sr from vehicle interior sound acquiring section 101, acquires accumulated vehicle interior sound $Sa_n$ from vehicle interior sound accumulating section 103, and acquires ambient sound Se from ambient sound isolating section 104. Sound pressure change determining section 301 calculates frequency distribution (vehicle interior sound frequency distribution) Fr of acquired vehicle interior sound Sr, frequency distribution (accumulated vehicle interior sound frequency distribution) $Fs_n$ of acquired accumulated vehicle interior sound $Sa_n$, and frequency distribution (ambient sound frequency distribution) Fe of acquired ambient sound Se.

Then, sound pressure change determining section 301 determines whether or not all magnitude relationships with thresholds (sound pressures of reference sound) in two or more particular frequency bands are the same between a candidate vehicle interior sound obtained by application of a sound pressure change specified based on records of vehicle interior sound up to the current time (for example, the magnitude relationships between accumulated vehicle interior sound and thresholds (reference sound) illustrated in FIG. 5), and ambient sound at the current time, during a predetermined period of time separated by timing controlled by switching time control section 302 (in other words, during passage of switching time T from the start of a timer).

In other words, if an ambient sound frequency distribution change (raising or attenuation) relative to an accumulated vehicle interior sound frequency distribution in each particular frequency band in a period one period before is included in a candidate sound pressure change method specified from an association relationship between the accumulated sound frequency distribution and candidate sound pressure change methods (for example, FIG. 5), sound pressure change determining section 301 outputs a reset instruction to switching time control section 302.

Switching time control section 302 (including time setting section 3021 and time control section 3022) basically has a function similar to that of switching time control section 102 (including time setting section 1021 and time control section 1022) (FIG. 1). Upon input of the reset instruction from sound pressure change determining section 301 (if sound pressure change determining section 301 determines that all the magnitude relationships with the thresholds in the respective particular frequency bands are the same), as in a case where the timer reaches zero, switching time control section 302 outputs a trigger signal to vehicle interior sound accumulating section 103 and sound pressure change setting section 105. In other words, switching time control section 302 resets a timing for sound pressure change setting section 105 to set a sound pressure change in each particular frequency band. In this case, the timing is provided for each predetermined period of time, to the current time.

Switching time control section 302 outputs the trigger signal to vehicle interior sound accumulating section 103 and sound pressure change setting section 105 and resets the timer, and calculates switching time T again and starts the timer. In other words, where the timer reaches zero or a reset instruction is input, switching time control section 302 outputs a trigger signal, resets the timer, and starts the timer using new switching time T.

Sound pressure change setting section 105 performs processing for setting a sound pressure change method at each timing of input of a trigger signal (in other words, timing controlled by switching time control section 302). However, if the timing for a trigger signal is reset based on a reset instruction from sound pressure change determining section 301, sound pressure change setting section 105 does not set a sound pressure change method.

Next, an example of a method for determining a sound pressure change in sound pressure change determining section 301 will be described with reference to FIG. 14.

Figure 14:
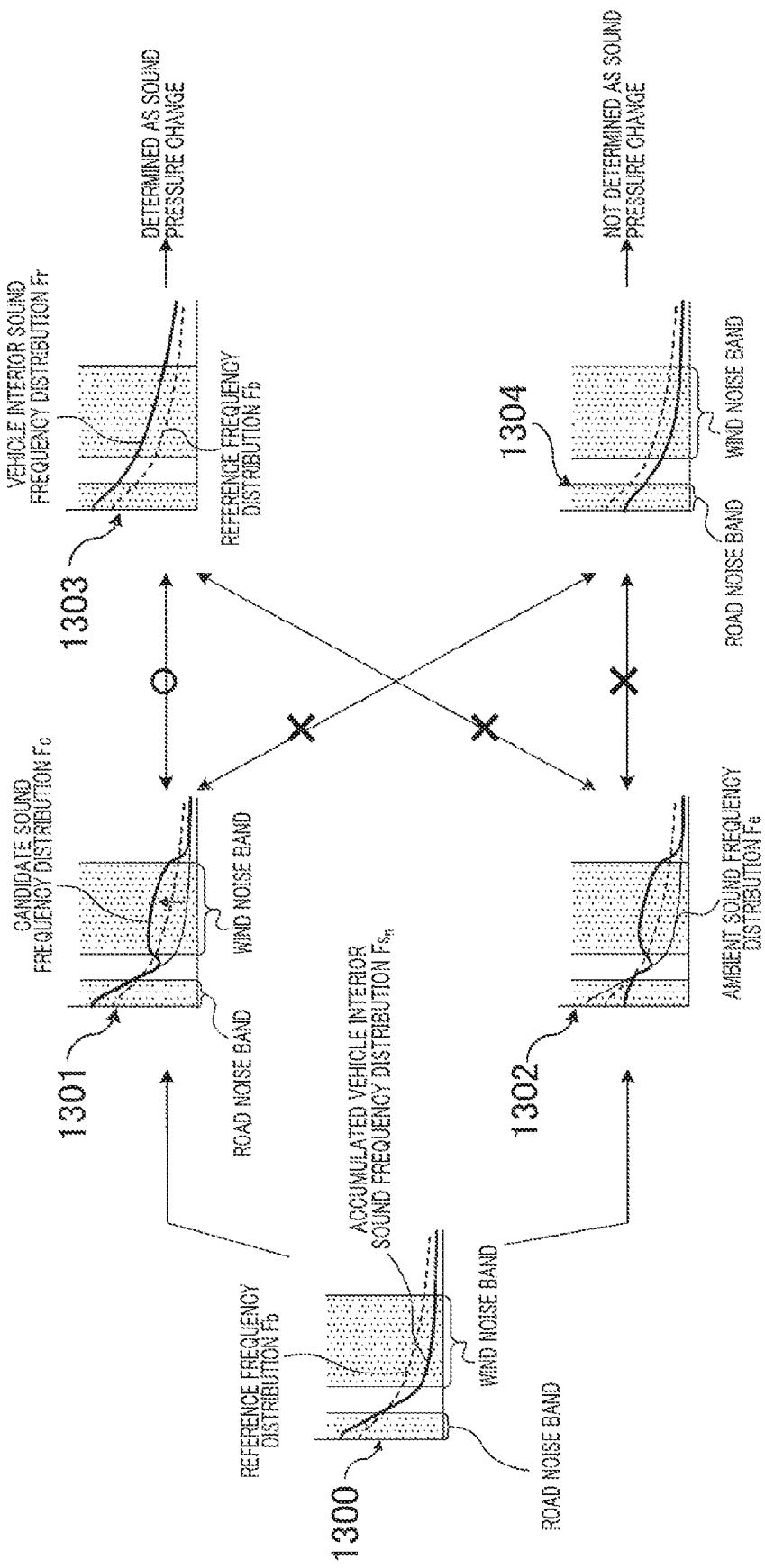
FIG. 14 is a diagram provided for description of processing in a sound pressure change determining section according to Embodiment 3 of the present invention.

Graph 1300 in FIG. 14 indicates an example of a relationship between accumulated vehicle interior sound frequency distribution $Fs_n$ accumulated at a current time in vehicle interior sound accumulating section 103 and reference frequency distribution Fb. In graph 1300 in FIG. 14, a sound pressure in a road noise band in accumulated sound frequency distribution $Fs_n$ is large and a sound pressure in a wind noise band is small relative to sound pressures (thresholds) in reference frequency distribution Fb.

Where a state at the current time is one indicated by graph 1300 in FIG. 14, candidate vehicle interior sounds obtained by application of a sound pressure change specified based on records of vehicle interior sound up to the current time include candidate sound (1301) obtained by application of a candidate sound pressure change method to raise the sound pressure in the wind noise band and not change the sound pressure in the road noise band, and candidate sound (1302) obtained by application of a candidate sound pressure change method to raise the sound pressure in the wind noise band and attenuate the sound pressure in the road noise band.

Also, graphs 1303 and 1304 in FIG. 14 each indicate an example of a relationship between vehicle interior sound frequency distribution Fr acquired by vehicle interior sound acquiring section 101 at the current time (that is, a frequency distribution of sound resulting from combination of control sound Sc generated in a period one period before and ambient sound Se at the current time) and reference frequency distribution Fb.

For example, in graph 1303 in FIG. 14, both a sound pressure in the road noise band and a sound pressure in the wind noise band in vehicle interior sound frequency distribution Fr are large relative to reference frequency distribution Fb. In other words, as illustrated in FIG. 14, all magnitude relationships with reference frequency distribution Fb in the respective particular frequency bands are the same between vehicle interior sound frequency distribution Fr indicated in graph 1303 and candidate sound frequency distribution Fc indicated in graph 1301.

Consequently, if vehicle interior sound Sr acquired at the current time is sound indicated in graph 1303 in FIG. 14, sound pressure change determining section 301 determines that a sound pressure change in vehicle interior sound Sr is a change equivalent to a sound pressure change due to the system (sound pressure change attributed to wakefulness-maintaining apparatus 300). In other words, sound pressure change determining section 301 determines that the sound pressure change to graph 1303 in FIG. 14 (sound pressure change attributed to a change in surrounding environment) and sound pressure change (1301) that would be obtained by reproduction of control sound wakefulness-maintaining apparatus 300 generates for each predetermined period of time (each timing for generating a trigger signal) are changes equivalent to each other. In other words, sound pressure change determining section 301 determines that the sound pressure change to graph 1303 in FIG. 14 is a sound pressure change that is sufficient to maintain wakefulness of a driver. Then, sound pressure change determining section 301 outputs a reset instruction to switching time control section 302. As described above, as a result of occurrence of the sound pressure change to graph 1303 in FIG. 14, sound pressure change determining section 301 determines that sound pressure change (1301) to be performed by wakefulness-maintaining apparatus 300 is not needed, and provides an instruction to reset the timer to switching time control section 302 even during the predetermined period of time (in the middle of operation of the timer).

Upon input of the reset instruction, switching time control section 302 outputs a trigger signal to sound pressure change setting section 105. However, if a trigger signal resulting from a reset instruction is input, sound pressure change setting section 105 does not need to make a sound pressure change to ambient sound, and thus, sets no sound pressure change method.

Meanwhile, for example, in graph 1304 in FIG. 14, both the sound pressure in the road noise band and the sound pressure in the wind noise band in vehicle interior sound frequency distribution Fr are small relative to reference frequency distribution Fb. In other words, as illustrated in FIG. 14, not all magnitude relationships with reference frequency distribution Fb in the respective particular frequency bands are the same between vehicle interior sound frequency distribution Fr indicated in graph 1304 and candidate sound frequency distribution Fc indicated in graph 1301 or 1302.

Consequently, if vehicle interior sound Sr acquired at the current time is sound indicated in graph 1304 in FIG. 14, sound pressure change determining section 301 determines that a sound pressure change in vehicle interior sound Sr is a change different from a sound pressure change by the system (sound pressure change attributed to wakefulness-maintaining apparatus 300). In other words, sound pressure change determining section 301 determines a sound pressure change to graph 1304 in FIG. 14 (sound pressure change attributed to change in surrounding environment) and a sound pressure change (1301 or 1302) that would be obtained by reproduction of control sound wakefulness-maintaining apparatus 300 generates for each predetermined period of time (each timing for generating a trigger signal) are different from each other. In other words, sound pressure change determining section 301 determines that the sound pressure change to graph 1304 in FIG. 14 is not a sound pressure change sufficient to maintain wakefulness of a driver. In such case, sound pressure change determining section 301 determines that the sound pressure change (1301 or 1302) by wakefulness-maintaining apparatus 300 should be performed, and does not output a reset instruction to switching time control section 302.

Figure 15:
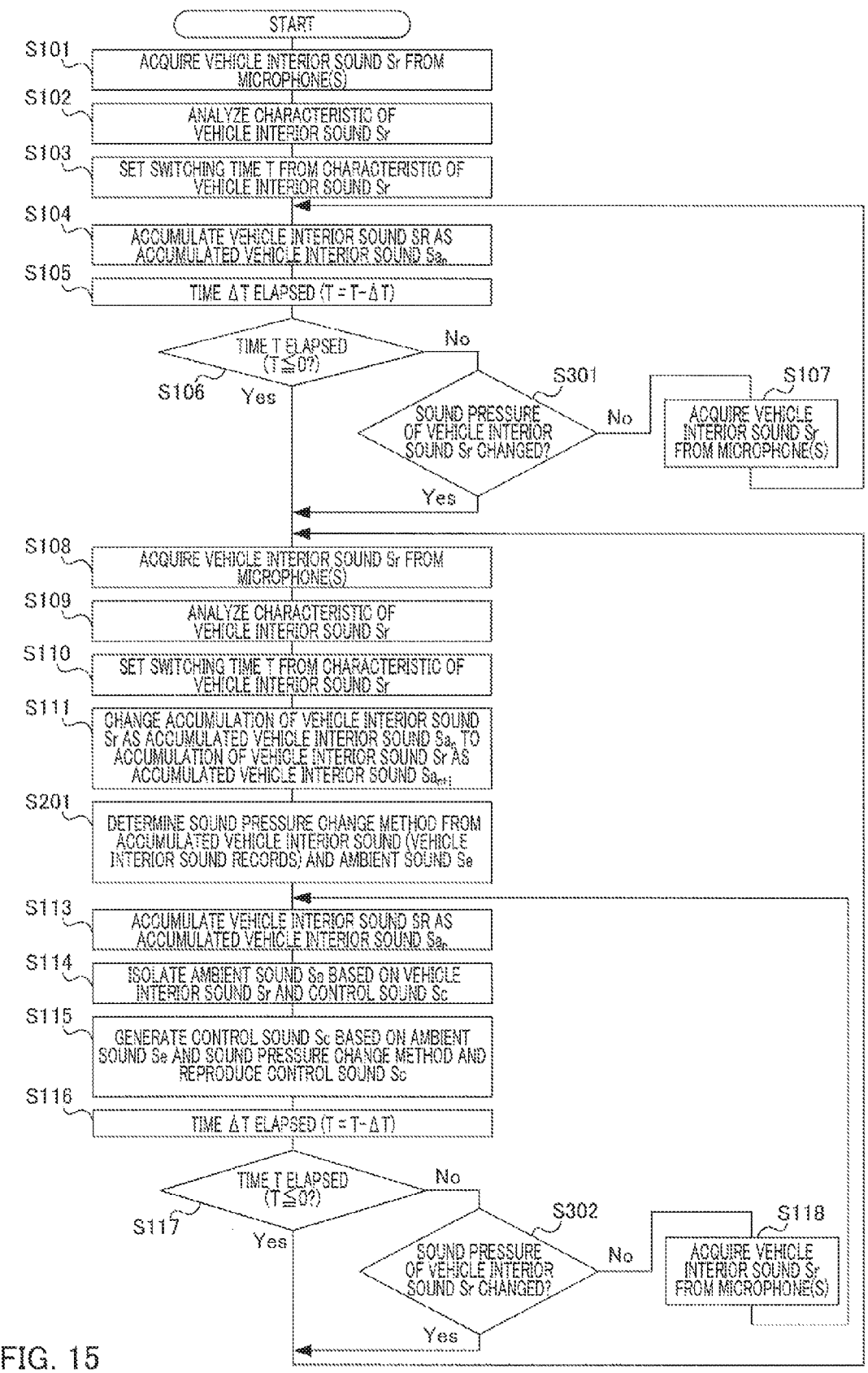
FIG. 15 is a flowchart provided for description of operation of the wakefulness-maintaining apparatus according to Embodiment 3 of the present invention.

Next, the flow of processing in wakefulness-maintaining apparatus 300 will be described. FIG. 15 is a flowchart provided for description of operation of wakefulness-maintaining apparatus 300. In FIG. 15, processing steps that are the same as those in Embodiment 2 (FIG. 12) are provided with reference numerals that are the same as those in Embodiment 2, and a description thereof will be omitted to avoid overlap.

In FIG. 15, if switching time T updated in step S105 is not zero or smaller (No in step S106), in step S301, sound pressure change determining section 301 determines whether or not a sound pressure change in vehicle interior sound Sr at a current time, which has been acquired in step S101, is a change sufficient to maintain wakefulness of a driver. In other words, sound pressure change determining section 301 determines whether or not all magnitude relationships with thresholds (sound pressures of reference sound) in the particular frequency bands are the same between vehicle interior sound Sr at the current time and candidate sound to be obtained by applying a sound pressure change specified based on records of vehicle interior sound up to the current time to ambient sound.

If it is determined that the sound pressure change in vehicle interior sound Sr at the current time is a change sufficient to maintain wakefulness of the driver (Yes in step S301), sound pressure change determining section 301 outputs a reset instruction to switching time control section 302, switching time control section 302 resets the timer, and in step S108, vehicle interior sound acquiring section 101 acquires vehicle interior sound Sr, in step S109, switching time control section 102 analyzes characteristics of vehicle interior sound Sr, and in step S110, switching time control section 102 sets new switching time T based on the characteristics of the vehicle interior sound Sr. Meanwhile, if it is not determined that the sound pressure change in vehicle interior sound Sr at the current time is a change sufficient to maintain wakefulness of the driver (No in step S301), in step S107, vehicle interior sound acquiring section 101 acquires vehicle interior sound Sr and the processing returns to step S104.

Also, in step S302, wakefulness-maintaining apparatus 300 performs processing similar to that in step S301.

Here, the present embodiment and Embodiment 1 are compared. As described above, a sound pressure is changed by means of wakefulness-maintaining apparatus for each predetermined period of time (each elapse of switching time T) and the sound pressure is also changed by a change in surrounding environment of a driver. In such case, in Embodiment 1, a sound pressure change occurs at each of a timing of elapse of switching time T (timing of generating a trigger signal) and a timing of generation of a change in surrounding environment. Thus, a change in sound pressure of vehicle interior sound a driver hears frequently occurs, resulting in an increase in annoyance to the driver.

On the other hand, wakefulness-maintaining apparatus 300 according to the present embodiment determines that a timing of a change in a sound pressure of ambient sound (vehicle interior sound a driver hears) Sr changed due to a change in surrounding environment, the change being equivalent to or more than a change made for a sound pressure of expected next vehicle interior sound by sound pressure change processing in wakefulness-maintaining apparatus 300 is the same timing as that of switching sound characteristics by wakefulness-maintaining apparatus 300. In such case, wakefulness-maintaining apparatus 300 resets a timing for setting a sound pressure change (in other words, switching time T), and changes targets in which vehicle interior sound Sr is accumulated.

Also, if the timing is reset, wakefulness-maintaining apparatus 300 sets no sound pressure change at the timing. Consequently, unnecessary sound pressure change processing in wakefulness-maintaining apparatus 300 can be prevented.

Consequently, according to the present embodiment, compared to cases where a change in sound pressure due to a change in surrounding environment is not considered (for example, Embodiment 1), the number of changes in sound pressure of vehicle interior sound a driver hears can be reduced, enabling annoyance to a driver to be avoided.

Although the present embodiment has been described in terms of a case where wakefulness-maintaining apparatus 300 sets a sound pressure change method in the same manner as wakefulness-maintaining apparatus 100 (FIG. 1) in Embodiment 1 does, wakefulness-maintaining apparatus 300 may set a sound pressure change method in the same manner as wakefulness-maintaining apparatus 200 (FIG. 7) in Embodiment 2 does.

Each embodiment of the present invention has been described thus far.

Although the foregoing embodiments have been described for the example of hardware implementation of the present invention, the present invention can be implemented with software, in concert with hardware.

Each of the functional blocks used in the descriptions of the embodiments are realized typically by LSI (large-scale integration), which is an integrated circuit. The functional blocks may each be a separate single chip, or some or all of the functional blocks may be collectively made into a single chip. The term "LSI" is used herein but the integrated circuit may be called an IC (integrated circuit), a system LSI device, a super-LSI device, or an ultra-LSI device depending on a difference in the degree of integration.

In addition, the integrated circuit is not limited to LSI and may be implemented by a dedicated circuit or by a general-purpose processor. In addition, an FPGA (field programmable gate array), which is programmable, or a reconfigurable processor that allows reconfiguration of connections or settings of the circuit cells in LSI may be used after the production of LSI.

Additionally, in the event of emergence of technology for circuit integration that replaces LSI technology by advancements in semiconductor technology or technology derivative therefrom, such technology may be used to integrate the functional blocks. Biotechnology may be applied, for example.

The disclosure of Japanese Patent Application No. 2011-109201, filed on May 16, 2011, including the specification, drawings, and abstract, is incorporated herein by reference in its entirety.

INDUSTRIAL APPLICABILITY

The present invention is useful for maintaining wakefulness of a driver by determining a method for changing sound characteristics in consideration of sound the driver has been hearing until then, in order to reliably make the driver perceive the change in characteristics of the sound.

REFERENCE SIGNS LIST 100, 200, 300 Wakefulness-maintaining apparatus
101 Vehicle interior sound acquiring section
102, 302 Switching time control section
1021, 3021 Time setting section
1022, 3022 Time control section
103 Vehicle interior sound accumulating section
104 Ambient sound isolating section
105, 201 Sound pressure change setting section
1051, 2011 Comparison section
1052, 2012 Setting section
106 Control sound generating section
107 Control sound reproducing section
301 Sound pressure change determining section

The invention claimed is:

1. A wakefulness-maintaining apparatus for maintaining wakefulness of a person, the apparatus comprising:
an analysis section that analyzes a characteristic of heard sound acquired via a microphone installed inside a vehicle, the heard sound containing control sound reproduced by the wakefulness-maintaining apparatus and ambient sound around the person in a state in which the control sound is not reproduced;
an accumulation section that accumulates the heard sound analyzed by the analysis section;
a setting section that sets a control method to be applied to the ambient sound, based on the characteristic of the heard sound accumulated by the accumulation section; and
a generation section that generates the control sound by applying the control method set by the setting section to the ambient sound.

2. The wakefulness-maintaining apparatus according to claim 1, further comprising a comparison section that compares sound pressures in two or more particular frequency bands of the heard sound with respective thresholds set in advance, and thereby determines a magnitude relationship between the sound pressure in each of the particular frequency bands and a corresponding one of the thresholds, wherein the control method to be applied to the ambient sound by the setting section includes setting a sound pressure change in each of the particular frequency bands according to a record of the magnitude relationship in the particular frequency band of the heard sound accumulated by the accumulation section.

3. The wakefulness-maintaining apparatus according to claim 2, wherein:

the record of the magnitude relationship is represented by a pattern of the magnitude relationship in each one of periods separated by sound familiarity obtainment time which is a period of time until the person becomes familiar with the heard sound;

the control method to be applied to the ambient sound by the setting section includes setting a sound pressure change in each of the particular frequency bands based on an association relationship in which candidates for the pattern are associated with respective candidate sound pressure changes; and in the association relationship, a pattern in which a sound pressure in any one of the particular frequency bands in a period one period before a current time is smaller than the corresponding threshold is associated with a candidate sound pressure change that increases the sound pressure in the particular frequency band.

4. The wakefulness-maintaining apparatus according to claim 3, wherein in the association relationship, in a particular frequency band whose sound pressure in the period one period before the current time is equal to or larger than the threshold among the two or more particular frequency bands, a pattern in which a sound pressure in a period two periods before the current time is smaller than the threshold is associated with a candidate sound pressure change that does not change the sound pressure in the particular frequency band, and a pattern in which the sound pressure in the period two period before is equal to or larger than the threshold is associated with a candidate sound pressure change that reduces the sound pressure in the particular frequency band.

5. The wakefulness-maintaining apparatus according to claim 2, wherein:

the comparison section determines the magnitude relationship in each of the particular frequency bands for each one of periods separated by sound familiarity obtainment time which is a period of time until the person becomes familiar with the heard sound; and the control method to be applied to the ambient sound by the setting section includes, from among the two or more particular frequency bands, increasing a sound pressure in a first frequency band in which the sound pressure in a period one period before a current time is smaller than the corresponding threshold, and changing a sound pressure in a second frequency band in which the sound pressure in the period one period before the current time is equal to or larger than the corresponding threshold, based on the sound pressure of the heard sound in a period two or more periods before the current time.

6. The wakefulness-maintaining apparatus according to claim 5, wherein the control method to be applied to the ambient sound by the setting section includes not changing a sound pressure in the second frequency band that is smaller than the corresponding threshold in the period two periods before, and reducing a sound pressure in the second frequency band that is equal to or larger than the corresponding threshold in the period two periods before.

7. The wakefulness-maintaining apparatus according to claim 5, wherein the control method to be applied to the ambient sound by the setting section includes setting a sound pressure change in the second frequency band so that at least one of the magnitude relationship in the first frequency band and the magnitude relationship in the second frequency band is different between the heard sound in the period two periods before and candidate heard sound obtained by application of a sound pressure change in the first frequency band to the ambient sound, the sound pressure change in the first frequency band being set based on the magnitude relationship in the period one period before.

8. The wakefulness-maintaining apparatus according to claim 2, further comprising;

a control section that controls a timing for the setting section to set a sound pressure change in each of the particular frequency bands, the timing being provided for each predetermined period of time; and a determination section that determines whether or not all the magnitude relationships in the respective particular frequency bands are the same between candidate heard sound to be obtained by application of a sound pressure change specified based on a record of the heard sound up to a current time and the ambient sound at the current time, during the predetermined period of time, wherein:

if the determination section determines that all the magnitude relationships in the respective particular frequency bands are the same, the control section resets the timing to the current time; and the setting section does not perform the sound pressure change setting at the timing reset by the control section, if a result of determination by the determination section is that all the magnitude relationships in the respective particular frequency bands are the same.

9. The wakefulness-maintaining apparatus according to claim 1, further comprising:

a time setting section that sets sound familiarity obtainment time which is a period of time until the person becomes familiar with the heard sound, based on time set in advance or the characteristic of the heard sound analyzed by the analysis section; and a time control section that controls the sound familiarity obtainment time set by the time setting section as a timing for the setting section to set the control method to be applied to the ambient sound, wherein the setting section sets the control method to be applied to the ambient sound, at the timing set by the time control section.

10. The wakefulness-maintaining apparatus according to claim 9, further comprising a sensitivity estimating section that estimates a sensitivity of the person that hears the heard sound to the heard sound, wherein the sound familiarity obtainment time set by the time setting section is adjusted according to the sensitivity of the person to the heard sound, the sensitivity being estimated by the sensitivity estimating section.

11. The wakefulness-maintaining apparatus according to claim 9, further comprising an experience determining section that determines a hearing experience of the person with respect to the ambient sound and the heard sound, wherein the sound familiarity obtainment time set by the time setting section is adjusted according to the hearing experience of the person with respect to at least one of the ambient sound and the heard sound, the hearing experience being determined by the experience determining section.

12. The wakefulness-maintaining apparatus according to claim 1, wherein:
the ambient sound is running noise generated while the vehicle is running; and
the heard sound is vehicle interior sound that the person hears in an interior of the vehicle.

13. A wakefulness-maintaining method for maintaining wakefulness of a person, the method comprising:
analyzing a characteristic of heard sound acquired via a microphone installed inside a vehicle, the heard sound containing control sound generated by the wakefulness-maintaining method and ambient sound around the person in a state in which the control sound is not reproduced;
accumulating the heard sound analyzed by the analysis;
setting a control method to be applied to the ambient sound, based on the characteristic of the heard sound accumulated by the accumulation; and
generating the control sound by applying, to the ambient sound, the control method that is set in the setting of the control method.

* * * * *